(12) United States Patent
Hanuka et al.

(10) Patent No.: US 8,821,465 B2
(45) Date of Patent: Sep. 2, 2014

(54) DISPOSABLE OSTOMY ASSEMBLIES

(71) Applicant: Stimatix GI Ltd., Misgav Business Park (IL)

(72) Inventors: David Hanuka, Ramat-Yishai (IL); Meir Or, Kfar Eshchar (IL)

(73) Assignee: Stimatix GI Ltd., Misgav Business Park (IL)

( * ) Notice: Subject to any disclaimer, the term of this patent is extended or adjusted under 35 U.S.C. 154(b) by 0 days.

(21) Appl. No.: 13/680,169

(22) Filed: Nov. 19, 2012

(65) Prior Publication Data

US 2013/0079737 A1    Mar. 28, 2013

Related U.S. Application Data

(60) Division of application No. 13/666,513, filed on Nov. 1, 2012, which is a continuation of application No. PCT/IB2011/051938, filed on May 2, 2011, and a continuation-in-part of application No. PCT/IL2010/000565, filed on Jul. 14, 2010.

(60) Provisional application No. 61/330,359, filed on May 2, 2010, provisional application No. 61/431,084, filed on Jan. 10, 2011, provisional application No. 61/225,546, filed on Jul. 14, 2009, provisional application No. 61/330,359, filed on May 2, 2010.

(51) Int. Cl.
*A61F 5/44* (2006.01)
*A61F 5/442* (2006.01)

(52) U.S. Cl.
CPC ............... *A61F 5/44* (2013.01); *A61F 5/4407* (2013.01); *A61F 5/442* (2013.01)

USPC ............................................... 604/333

(58) Field of Classification Search
CPC .......... A61F 5/44; A61F 5/4407; A61F 5/442
USPC ............................................... 604/333
See application file for complete search history.

(56) References Cited

U.S. PATENT DOCUMENTS

| 2,243,529 A | 5/1941 | Grossman et al. |
| 2,341,984 A | 2/1944 | Graves |
| 2,510,766 A | 6/1950 | Surface |
| 2,544,579 A | 3/1951 | Ardner |
| 2,639,710 A | 5/1953 | Fazio |

(Continued)

FOREIGN PATENT DOCUMENTS

| CN | 1694661 | 11/2005 |
| DE | 19921555 | 2/2000 |

(Continued)

OTHER PUBLICATIONS

Official Action Dated Jan. 30, 2013 From the U.S. Patent and Trademark Office Re. U.S. Appl. No. 12/835,838.

(Continued)

*Primary Examiner* — Susan Su
*Assistant Examiner* — Guy K Townsend

(57) ABSTRACT

Disposable elements for use in ostomy. In one embodiment a cap with an integral bag is provided. In another embodiment a sealable bag is provided with means for sealing. In another embodiment, the ostomy port itself is disposable.

58 Claims, 15 Drawing Sheets

(56) References Cited

U.S. PATENT DOCUMENTS

| | | | |
|---|---|---|---|
| 2,667,167 A | 1/1954 | Raiche | |
| 2,971,510 A | 2/1961 | Berger | |
| 3,398,744 A | 8/1968 | Hooper | |
| 3,447,533 A | 6/1969 | Spicer | |
| 3,718,141 A | 2/1973 | Goetz | |
| 3,976,076 A | 8/1976 | Beach | |
| 4,030,500 A | 6/1977 | Ronnquist | |
| 4,121,589 A | 10/1978 | McDonnell | |
| 4,170,231 A | 10/1979 | Collins | |
| 4,183,357 A | 1/1980 | Bentley et al. | |
| 4,209,010 A | 6/1980 | Ward et al. | |
| 4,210,131 A | 7/1980 | Perlin | |
| 4,232,672 A | 11/1980 | Steer et al. | |
| 4,265,244 A | 5/1981 | Hill | |
| 4,338,937 A | 7/1982 | Lerman | |
| 4,344,434 A | 8/1982 | Robertson | |
| 4,351,322 A | 9/1982 | Prager | |
| 4,381,765 A | 5/1983 | Burton | |
| 4,399,809 A | 8/1983 | Baro et al. | |
| 4,534,761 A | 8/1985 | Raible | |
| 4,634,421 A | 1/1987 | Hegemann | |
| 4,642,107 A | 2/1987 | Arnone et al. | |
| 4,662,890 A | 5/1987 | Burton et al. | |
| 4,721,508 A | 1/1988 | Burton | |
| 4,786,283 A | 11/1988 | Andersson | |
| 4,804,375 A | 2/1989 | Robertson | |
| 4,810,250 A | 3/1989 | Ellenberg et al. | |
| 4,854,316 A | 8/1989 | Davis | |
| 4,941,869 A | 7/1990 | D'Amico | |
| 4,950,223 A | 8/1990 | Silvanov | |
| 4,981,465 A | 1/1991 | Ballan et al. | |
| 5,004,464 A | 4/1991 | Leise, Jr. | |
| 5,026,360 A | 6/1991 | Johnson et al. | |
| 5,045,052 A | 9/1991 | Sans | |
| 5,108,430 A | 4/1992 | Ravo | |
| 5,125,916 A | 6/1992 | Panebianco et al. | |
| 5,135,519 A | 8/1992 | Helmer | |
| 5,163,897 A | 11/1992 | Persky | |
| 5,163,930 A | 11/1992 | Blum | |
| 5,261,898 A | 11/1993 | Polin et al. | |
| 5,269,774 A | 12/1993 | Gray | |
| 5,501,678 A | 3/1996 | Olsen | |
| 5,549,588 A | 8/1996 | Johnson | |
| 5,569,216 A | 10/1996 | Kim | |
| 5,658,266 A | 8/1997 | Colacello et al. | |
| 5,683,372 A | 11/1997 | Colacello et al. | |
| 5,771,590 A | 6/1998 | Colacello et al. | |
| 5,785,677 A | 7/1998 | Auweiler | |
| 5,947,942 A * | 9/1999 | Galjour | 604/345 |
| 6,033,390 A | 3/2000 | Von Dyck | |
| 6,050,982 A | 4/2000 | Wheeler | |
| 6,329,465 B1 | 12/2001 | Takahashi et al. | |
| 6,350,255 B1 * | 2/2002 | von Dyck | 604/338 |
| 6,357,445 B1 | 3/2002 | Shaw | |
| 6,481,589 B2 | 11/2002 | Blomdahl et al. | |
| 6,485,476 B1 | 11/2002 | Von Dyck et al. | |
| 6,595,971 B1 * | 7/2003 | von Dyck et al. | 604/334 |
| 6,659,988 B1 | 12/2003 | Steer et al. | |
| 6,689,111 B2 | 2/2004 | Mulhauser et al. | |
| 6,695,825 B2 | 2/2004 | Castles | |
| 6,723,079 B2 | 4/2004 | Cline | |
| 6,963,772 B2 | 11/2005 | Bloom et al. | |
| 7,001,367 B2 | 2/2006 | Arkinstall | |
| 7,083,569 B2 * | 8/2006 | Boulanger et al. | 600/32 |
| 7,087,041 B2 | 8/2006 | Von Dyck et al. | |
| 7,250,040 B2 * | 7/2007 | Andersen | 604/343 |
| 7,314,443 B2 | 1/2008 | Jordan et al. | |
| 7,582,072 B2 | 9/2009 | McMichael | |
| 7,670,289 B1 | 3/2010 | McCall | |
| 7,857,796 B2 | 12/2010 | Cline et al. | |
| 8,070,737 B2 | 12/2011 | Cline et al. | |
| 8,092,437 B2 | 1/2012 | Cline | |
| 8,100,875 B2 | 1/2012 | Cline et al. | |
| 8,142,406 B2 | 3/2012 | Blum | |
| 8,388,586 B2 | 3/2013 | Weig | |
| 8,460,259 B2 | 6/2013 | Tsai | |
| 2003/0199783 A1 | 10/2003 | Bloom et al. | |
| 2003/0220621 A1 | 11/2003 | Arkinstall | |
| 2004/0029467 A1 | 2/2004 | Lacroix | |
| 2004/0073179 A1 | 4/2004 | Andersen | |
| 2004/0122527 A1 | 6/2004 | Imran | |
| 2004/0167376 A1 | 8/2004 | Peters et al. | |
| 2004/0181197 A1 | 9/2004 | Cline | |
| 2005/0027159 A1 | 2/2005 | Feng et al. | |
| 2005/0054996 A1 | 3/2005 | Gregory | |
| 2005/0065488 A1 | 3/2005 | Elliott | |
| 2005/0104457 A1 | 5/2005 | Jordan et al. | |
| 2006/0048283 A1 | 3/2006 | Sorensen | |
| 2006/0206069 A1 | 9/2006 | Cline | |
| 2006/0229596 A1 | 10/2006 | Weiser et al. | |
| 2007/0049878 A1 | 3/2007 | Kim et al. | |
| 2007/0088300 A1 | 4/2007 | Cline et al. | |
| 2007/0142780 A1 | 6/2007 | Van Lue | |
| 2007/0191794 A1 | 8/2007 | Cline et al. | |
| 2007/0219532 A1 | 9/2007 | Karpowicz et al. | |
| 2007/0276346 A1 | 11/2007 | Poulsen et al. | |
| 2008/0033380 A1 | 2/2008 | Andersen | |
| 2008/0091154 A1 | 4/2008 | Botten | |
| 2008/0108862 A1 * | 5/2008 | Jordan et al. | 600/30 |
| 2008/0135044 A1 | 6/2008 | Freitag et al. | |
| 2008/0269698 A1 | 10/2008 | Alexander et al. | |
| 2008/0275410 A1 | 11/2008 | Burt | |
| 2009/0043151 A1 | 2/2009 | Gobel | |
| 2009/0247969 A1 | 10/2009 | Nishtala et al. | |
| 2010/0069859 A1 | 3/2010 | Weig | |
| 2010/0174253 A1 | 7/2010 | Cline et al. | |
| 2011/0015475 A1 | 1/2011 | Hanuka et al. | |
| 2011/0040231 A1 | 2/2011 | Gregory | |
| 2011/0106032 A1 * | 5/2011 | Kratky | 604/337 |
| 2012/0136324 A1 | 5/2012 | Hanuka et al. | |
| 2013/0060212 A1 | 3/2013 | Hanuka et al. | |
| 2013/0060213 A1 | 3/2013 | Hanuka et al. | |
| 2013/0079736 A1 | 3/2013 | Hanuka et al. | |
| 2013/0079738 A1 | 3/2013 | Hanuka et al. | |
| 2013/0116642 A1 | 5/2013 | Hanuka et al. | |
| 2013/0304008 A1 | 11/2013 | Hanuka et al. | |

FOREIGN PATENT DOCUMENTS

| | | | |
|---|---|---|---|
| DE | 102007062133 | 7/2009 | |
| EP | 1795157 | 6/2007 | |
| EP | 2027835 | 2/2009 | |
| GB | 2094153 | 9/1982 | |
| JP | 2006-314479 | 11/2006 | |
| JP | 2008-507308 | 3/2008 | |
| WO | WO 87/03192 | 6/1987 | |
| WO | WO 90/07311 | 7/1990 | |
| WO | WO 96/32904 | 10/1996 | |
| WO | WO 99/43277 | 9/1999 | |
| WO | WO 01/49224 | 7/2001 | |
| WO | WO 02/058603 | 8/2002 | |
| WO | WO 03/065945 | 8/2003 | |
| WO | WO 03/071997 | 9/2003 | |
| WO | WO 2006/010556 | 2/2006 | |
| WO | WO 2008/048856 | 4/2008 | |
| WO | WO 2008/103789 | 8/2008 | |
| WO | WO 2008/141180 | 11/2008 | |
| WO | WO 2009/083183 | 7/2009 | |
| WO | WO2009083183 * | 7/2009 | A61F 5/445 |
| WO | WO 2009/155537 | 12/2009 | |
| WO | WO 2011/007355 | 1/2011 | |
| WO | WO 2011/013872 | 2/2011 | |
| WO | WO 2011/039517 | 4/2011 | |
| WO | WO 2011/138727 | 11/2011 | |
| WO | WO 2011/138728 | 11/2011 | |
| WO | WO 2011/138731 | 11/2011 | |
| WO | WO 2013/168165 | 11/2013 | |

OTHER PUBLICATIONS

Official Action Dated Mar. 25, 2013 From the US Patent and Trademark Office Re. U.S. Appl. No. 13/666,178.

(56) References Cited

OTHER PUBLICATIONS

Communication Pursuant to Article 94(3) EPC Dated Feb. 11, 2013 From the European Patent Office Re. Application No. 10747082.5.
Official Action Dated Mar. 5, 2013 From the US Patent and Trademark Office Re. U.S. Appl. No. 13/666,513.
Official Action Dated May 9, 2013 From the US Patent and Trademark Office Re. U.S. Appl. No. 13/666,461.
Communication Relating to the Results of the Partial International Search Dated Aug. 12, 2011 From the International Searching Authority Re. Application No. PCT/IB2011/051932.
Communication Relating to the Results of the Partial International Search Dated Aug. 16, 2011 From the International Searching Authority Re. Application No. PCT/IB2011/051933.
Communication Relating to the Results of the Partial International Search Dated Nov. 17, 2010 From the International Searching Authority Re. Application No. PCT/IL2010/000565.
Communication Relating to the Results of the Partial International Search Dated Aug. 18, 2011 From the International Searching Authority Re: Application No. PCT/IB2011/051938.
International Preliminary Report on Patentability Dated Jun. 1, 2012 From the International Preliminary Examining Authority Re. Application No. PCT/IB2011/051933.
International Preliminary Report on Patentability Dated Jun. 5, 2012 From the International Preliminary Examining Authority Re. Application No. PCT/IB2011/051932.
International Preliminary Report on Patentability Dated Sep. 6, 2012 From the International Preliminary Examining Authority Re. Application No. PCT/IB2011/051938.
International Preliminary Report on Patentability Dated Oct. 31, 2011 From the International Preliminary Examining Authority Re. Application No. PCT/IL2010/000565.
International Search Report and the Written Opinion Dated Oct. 14, 2011 From the International Searching Authority Re. Application No. PCT/IB2011/051933.
International Search Report and the Written Opinion Dated Oct. 17, 2011 From the International Searching Authority Re. Application No. PCT/IB2011/051932.
International Search Report and the Written Opinion Dated Aug. 18, 2011 From the International Searching Authority Re. Application No. PCT/IB2011/051936.
International Search Report and the Written Opinion Dated Oct. 19, 2011 From the International Searching Authority Re: Application No. PCT/IB2011/051938.
International Search Report and the Written Opinion Dated Feb. 28, 2011 From the International Searching Authority Re. Application No. PCT/IL2010/000565.
Invitation to Pay Additional Fees Dated Oct. 7, 2011 From the International Preliminary Examining Authority Re. Application No. PCT/IL2010/000565.
Notification Concerning Informal Communications With the Applicant Dated May 3, 2012 From the International Searching Authority Re: Application No. PCT/IB2011/051938.
Notification Concerning Informal Communications With the Applicant Dated May 4, 2012 From the International Searching Authority Re: Application No. PCT/IB2011/051933.
Notification Concerning Informal Communications With the Applicant Dated May 18, 2012 From the International Searching Authority Re: Application No. PCT/IB2011/051932.
Response Dated May 30, 2011 to the Written Opinion of Feb. 28, 2011 From the International Searching Authority Re. Application No. PCT/IL2010/000565.
Restriction Official Action Dated Oct. 15, 2012 From the US Patent and Trademark Office Re. U.S. Appl. No. 12/835,838.
Written Opinion Dated Jun. 1, 2012 From the International Preliminary Examining Authority Re. Application No. PCT/IB2011/051938.
International Preliminary Report on Patentability Dated Nov. 15, 2012 From the International Bureau of WIPO Re. Application No. PCT/IB2011/051936.
Applicant-Initiated Interview Summary Dated Jul. 25, 2013 From the US Patent and Trademark Office Re. U.S. Appl. No. 13/680,161.
Official Action Dated Jul. 1, 2013 From the US Patent and Trademark Office Re. U.S. Appl. No. 13/384,343.
Translation of Notification of Office Action Dated Jul. 30, 2013 From the State Intellectual Property Office of the People's Republic of China Re. Application No. 201080032032.X.
Official Action Dated Aug. 29, 2013 From the US Patent and Trademark Office Re. U.S. Appl. No. 12/835,838.
Applicant-Initiated Interview Summary Dated Jul. 26, 2013 From the US Patent and Trademark Office Re. U.S. Appl. No. 13/666,513.
Official Action Dated Jul. 11, 2013 From the US Patent and Trademark Office Re. U.S. Appl. No. 13/680,161.
Official Action Dated Nov. 7, 2013 From the US Patent and Trademark Office Re. U.S. Appl. No. 13/666,178.
Official Action Dated Nov. 13, 2013 From the US Patent and Trademark Office Re. U.S. Appl. No. 13/666,461.
Communication Relating to the Results of the Partial International Search Dated Sep. 16, 2013 From the International Searching Authority Re. Application No. PCT/IL2013/050401.
Official Action Dated Oct. 16, 2013 From the US Patent and Trademark Office Re. U.S. Appl. No. 13/666,244.
Official Action Dated Oct. 16, 2013 From the US Patent and Trademark Office Re. U.S. Appl. No. 13/666,513.
Official Action Dated Oct. 18, 2013 From the US Patent and Trademark Office Re. U.S. Appl. No. 13/384,343.
Zhang et al. "Occlusion Effect Comparison of Artificial Silicone Rubber Closure Devices With Different Diameters", Chinese Journal of Tissue Engineering Research, 16(8): 1496-1500, Feb. 19, 2012. Abstract in English.
Applicant-Initiated Interview Summary Dated Dec. 13, 2013 From the US Patent and Trademark Office Re. U.S. Appl. No. 13/666,244.
Applicant-Initiated Interview Summary Dated Dec. 13, 2013 From the US Patent and Trademark Office Re. U.S. Appl. No. 13/666,513.
Applicant-Initiated Interview Summary Dated Jan. 27, 2014 From the US Patent and Trademark Office Re. U.S. Appl. No. 13/384,343.
Communication Pursuant to Article 94(3) EPC Dated Dec. 17, 2013 From the European Patent Office Re. Application No. 11723672.9.
Communication Pursuant to Article 94(3) EPC Dated Dec. 19, 2013 From the European Patent Office Re. Application No. 11723674.5.
Communication Pursuant to Article 94(3) EPC Dated Dec. 19, 2013 From the European Patent Office Re. Application No. 11724783.3.
International Search Report and the Written Opinion Dated Dec. 20, 2013 From the International Searching Authority Re. Application No. PCT/IL2013/050401.
Official Action Dated Jan. 14, 2014 From the US Patent and Trademark Office Re. U.S. Appl. No. 13/680,161.
Summons to Attend Oral Proceedings Pursuant to Rule 115(1) EPC Dated Nov. 22, 2013 From the European Patent Office Re. Application No. 10747082.5.
Advisory Action Before the Filing of an Appeal Brief Dated Feb. 4, 2014 From U.S. Appl. No. 12/835,838.
Advisory Action Before the Filing of an Appeal Brief Dated Mar. 31, 2014 From U.S. Appl. No. 13/384,343.
Notice of Allowance Dated Feb. 18, 2014 From U.S. Appl. No. 13/666,513.
Notice of Allowance Dated Mar. 18, 2014 From U.S. Appl. No. 13/666,178.
Applicant-Initiated Interview Summary Dated Apr. 14, 2014 From U.S. Appl. No. 13/384,343.
Notice of Allowance Dated May 8, 2014 From U.S. Appl. No. 13/666,461.
Notice of Allowance Dated Apr. 29, 2014 From U.S. Appl. No. 13/680,161.
Notice of Reason for Rejection Dated Apr. 15, 2014 From the Japanese Patent Office Re. Application No. 2012-520149 and Its Translation Into English.

(56) References Cited

OTHER PUBLICATIONS

Notification of Office Action Dated May 6, 2014 From The State Intellectual Property Office of the People's Republic of China Re. Application No. 2011800331827 and Its Translation Into English.
Notification of Office Action Dated Apr. 18, 2014 From the State Intellectual Property Office of the People's Republic of China Re. Application No. 201080032032.X and Its Translation Into English.

Search Report Dated May 6, 2014 From The State Intellectual Property Office of the People's Republic of China Re. Application No. 2011800331827 and Its Translation Into English.

Search Report Dated Apr. 18, 2014 From the State Intellectual Property Office of the People's Republic of China Re. Application No. 201080032032.X and Its Translation Into English.

* cited by examiner

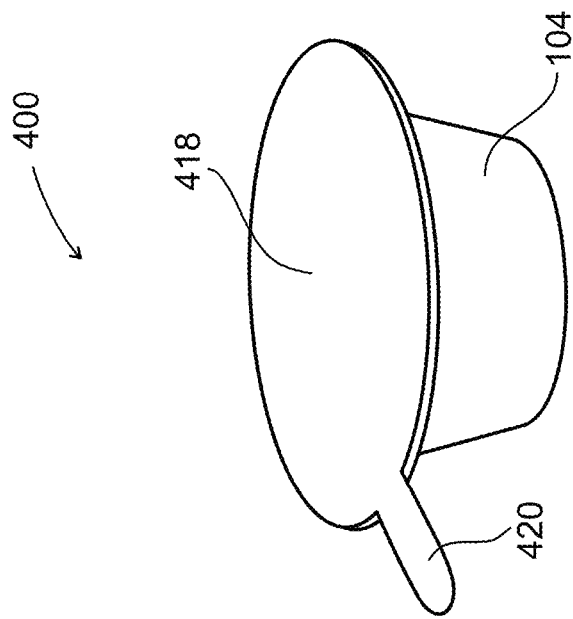
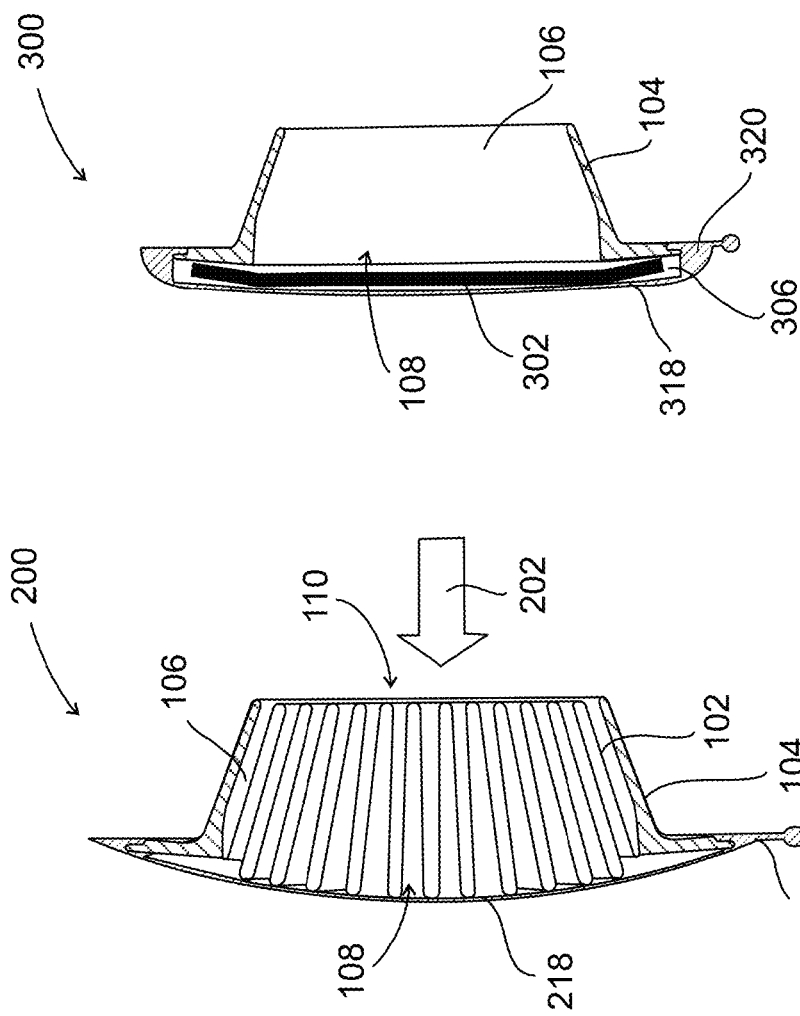
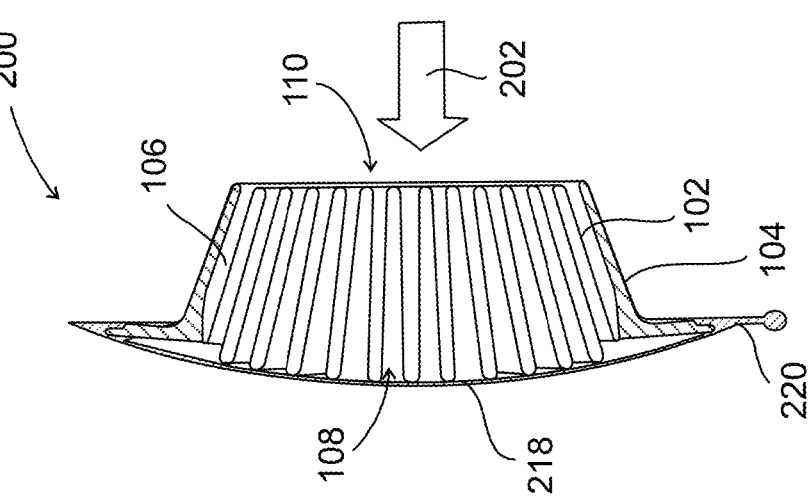
Figure 6
Figure 5
Figure 4

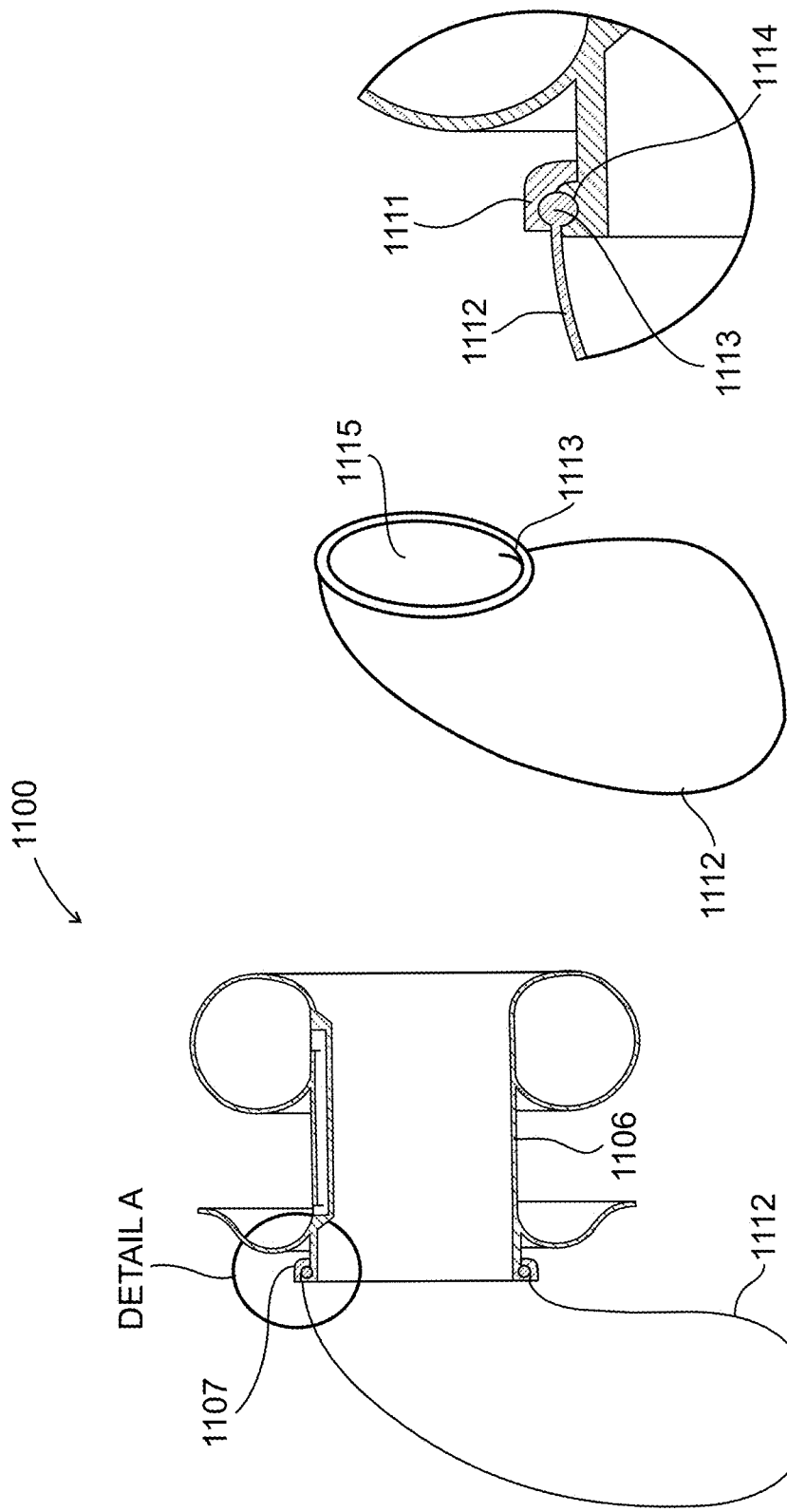

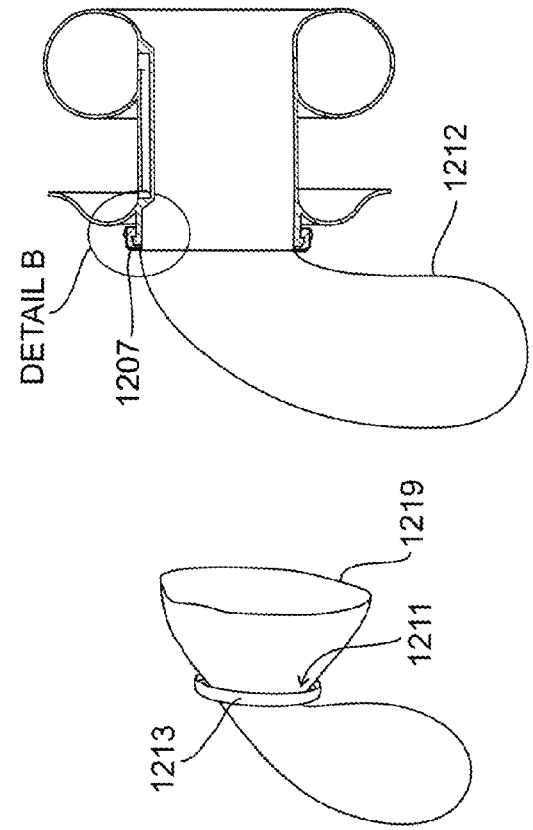
Figure 14C
Figure 14B
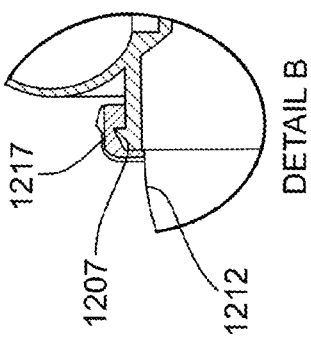
Figure 14D
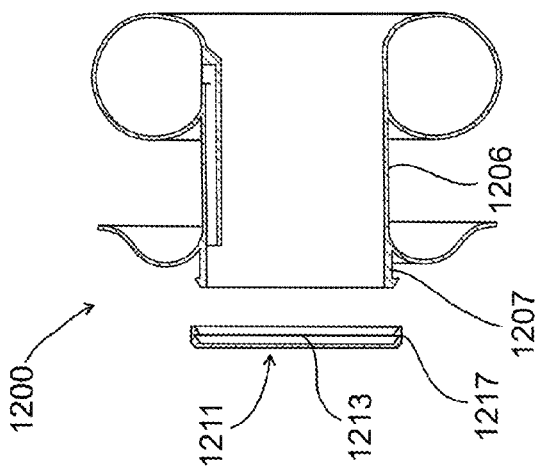
Figure 14A

DISPOSABLE OSTOMY ASSEMBLIES

RELATED APPLICATIONS

This application is a Divisional of U.S. patent application Ser. No. 13/666,513 filed on Nov. 1, 2012, which is a Continuation of PCT Patent Application No. PCT/IB2011/051938 filed on May 2, 2011, which claims the benefit of priority under 35 USC 119(e) of U.S. Provisional Patent Application Nos. 61/330,359 filed on May 2, 2010 and 61/431,084 filed on Jan. 10, 2011.

PCT Patent Application No. PCT/IB2011/051938 is also a Continuation-In-Part (CIP) of PCT Patent Application No. PCT/IL2010/000565 filed Jul. 14, 2010, which claims the benefit of priority under 35 USC §119(e) of U.S. Provisional Patent Application Nos. 61/225,546 filed on Jul. 14, 2009 and 61/330,359 filed on May 2, 2010. The contents of the above applications are all incorporated by reference as if fully set forth herein in their entirety.

PCT Patent Application No. PCT/IB2011/051938 is also related to PCT Patent Application Nos. PCT/IB2011/051932, PCT/IB2011/051936, and PCT/IB2011/051933, which were all filed by, inter alia, Applicant Stimatix GI Ltd., concurrently with PCT Patent Application No. PCT/IB2011/051938, the disclosures of which are incorporated herein by reference.

FIELD AND BACKGROUND OF THE INVENTION

The present invention, in some embodiments thereof, relates to ostomy ports and, more particularly, but not exclusively, to a disposable ostomy cap for use with ostomy ports and/or other parts, such as an ostomy bag or a whole port.

Following a stoma operation, an ostomy port may be inserted through the stoma for controlling discharge of waste content through the stoma. An ostomy bag may be attached to a proximal opening in the port into which the waste content is discharged. The bag may require replacing several times a day according to an amount of waste content accumulating in the bag.

As an alternative to having a bag attached at all times to the port, some ports are configured to be sealed by a cap at the proximal opening. In these ports, the waste content does not flow out the proximal opening until the cap is removed. Rather, the waste content accumulates inside the port until released by a user. Generally, the user of the ostomy port first attaches an ostomy bag or some other waste collection element to the port and only then removes the cap to allow waste content discharge into the bag.

In U.S. Pat. No. 6,033,390 von Dyck describes "a continent ostomy port device has a face plate defining an aperture alignable with the opening of a stoma in the user's body and a closure adjacent to the aperture is adapted to permit covering and uncovering of the aperture in the face plate. A catheter extends from one side of the face plate proximally, and one end of the catheter is disposed within the ostomy site when the port device is in use. The catheter has continuous exterior and interior side walls, the latter defining a major lumen and is sized and shaped for non-surgical insertion through a stoma to a sufficient distance that the presence of the catheter within the stoma provides a barrier which reduces the incidence of prolapse, without the use of extraneous, externally applied materials or additional surgery. A removable cartridge fits snugly and slideably within the major lumen of the catheter of the device so as to prevent inadvertent escape of body waste material from the stoma when the cartridge is in place, without use of an ostomy bag, and to clean the interior side wall of the catheter as the cartridge is pressed into the major lumen. An anti-reflux valve is activated to prevent escape of body waste and deactivated for passage of fluid. Retaining structure is connected to the catheter, and is non-surgically, snugly fittable into the stoma, to cause the port device to be self-retaining in a normal use position within a stoma, without surgery or fixation materials".

In U.S. Pat. No. 6,050,982 to Wheeler is described "A concealed colostomy apparatus comprising a sleeve insertable into the bowel via a discharge opening thereof for retention therein, the sleeve then having a discharge end; a cap removably interfitting the discharge end of the sleeve; and a flexible pouch received in collapsed position into the sleeve to in turn receive feces from the bowel, the cap being removable to allow distending of the pouch outside the sleeve and continued filling of fecal matter into the pouch."

Additional background art includes U.S. Pat. Nos. 4,121,589; 4,338,937; 4,634,421; 4,721,508; 4,381,765; and 4,662,890.

SUMMARY OF THE INVENTION

There is provided in accordance with an exemplary embodiment of the invention, a disposable cap for sealing a proximal opening in an ostomy port, including a coupler adapted to couple to an ostomy port and comprising a collapsed ostomy bag.

In an exemplary embodiment of the invention, the bag is housed in a body of the cap. Optionally or alternatively, the cap is wider at a proximal side thereof than at a distal side thereof.

In an exemplary embodiment of the invention, the cap is configured to extend less than 1 cm proximally from the port.

In an exemplary embodiment of the invention, the cap is configured to fit into the port.

In an exemplary embodiment of the invention, the cap is configured to interlock with an interlocking mechanism of the port.

In an exemplary embodiment of the invention, the bag is configured to deploy when a pressure in the port is above a threshold.

In an exemplary embodiment of the invention, the bag includes a pullable element for manual deployment.

In an exemplary embodiment of the invention, the bag includes a deployment prevention element.

In an exemplary embodiment of the invention, the cap includes a pressure indicator.

In an exemplary embodiment of the invention, the cap includes a sensing circuitry.

In an exemplary embodiment of the invention, the cap includes a foil seal.

In an exemplary embodiment of the invention, the cap includes a separately openable and closable cap-covering.

In an exemplary embodiment of the invention, the cap has a sleeve shaped body and wherein the cap-covering is configured to fit on two opposite sides of the body.

In an exemplary embodiment of the invention, the cap includes a separately openable cap-covering.

In an exemplary embodiment of the invention, the bag is elastic.

In an exemplary embodiment of the invention, the bag is integrally formed with the cap.

In an exemplary embodiment of the invention, the bag is permanently attached to the cap.

In an exemplary embodiment of the invention, the cap includes a closure for sealing the bag after filling thereof.

In an exemplary embodiment of the invention, the cap includes an adhesive attachment element for attaching the bag after deployment directly to a body of the patient.

In an exemplary embodiment of the invention, the bag has a volume when collapsed of less than 10 cc and when full of at least 300 cc.

There is provided in accordance with an exemplary embodiment of the invention, a method of using an ostomy port, comprising:

(a) determining that waste needs to be evacuated from the port;
(b) deploying a bag from the port without opening the port to outside of the bag;
(c) removing the bag with waste inside; and
(d) sealing the port.

In an exemplary embodiment of the invention, deploying a bag comprises opening a cover of a cap of the port.

In an exemplary embodiment of the invention, removing the bag comprises sealing the bag. Optionally, sealing the bag comprises sealing with a cover of the cap. Optionally or alternatively, sealing the bag comprises sealing by narrowing a portion of the bag. Optionally or alternatively, sealing the port comprises sealing with one or both of a collapsed bag and a cap. Alternatively, sealing the port comprises sealing without a bag.

There is provided in accordance with an exemplary embodiment of the invention, a disposable ostomy port comprising:

a tube insertable through a stoma into in an intestinal portion for conducting a flow of waste content from the intestinal portion; and
a retention balloon for affixing the tube to the stoma and configured for contact with tissue;
wherein the tube and the retention balloon are formed as a single component. Optionally, the port comprises a stomal cover formed as part of the single component.

There is provided in accordance with an exemplary embodiment of the invention, a disposable ostomy port including a waste tube and a lumen distally connected to the balloon for inflating the balloon therethrough with an inflation fluid and including an inflation valve.

In an exemplary embodiment of the invention, the tube includes a sealed proximal end.

In an exemplary embodiment of the invention, the port comprises a gas filtering mechanism.

In an exemplary embodiment of the invention, the tube includes an ostomy bag attached to a proximal end thereof.

In an exemplary embodiment of the invention, the tube has a proximal opening configured to attachment of an ostomy bag thereto.

There is provided in accordance with an exemplary embodiment of the invention, a sensing cap configured for attachment to an ostomy port opening and comprising at least one distensible element, which distends in response to a pressure in the port.

There is provided in accordance with an exemplary embodiment of the invention, an ostomy port adapted for insertion into the body and including a non-detachable waste bag.

There is provided in accordance with an exemplary embodiment of the invention, an ostomy bag coupled with a closure element for sealing thereof. Optionally, the bag has a rim for mounting on an ostomy port and wherein the closure element comprises a cap that fits on the rim. Optionally, the cap is configured to fit on either side of the rim. Optionally or alternatively, the closure element comprises a tie.

Unless otherwise defined, all technical and/or scientific terms used herein have the same meaning as commonly understood by one of ordinary skill in the art to which the invention pertains. Although methods and materials similar or equivalent to those described herein can be used in the practice or testing of embodiments of the invention, exemplary methods and/or materials are described below. In case of conflict, the patent specification, including definitions, will control. In addition, the materials, methods, and examples are illustrative only and are not intended to be necessarily limiting.

Implementation of the method and/or system of embodiments of the invention can involve performing or completing selected tasks manually, automatically, or a combination thereof. Moreover, according to actual instrumentation and equipment of embodiments of the method and/or system of the invention, several selected tasks could be implemented by hardware, by software or by firmware or by a combination thereof using an operating system.

For example, hardware for performing selected tasks according to embodiments of the invention could be implemented as a chip or a circuit. As software, selected tasks according to embodiments of the invention could be implemented as a plurality of software instructions being executed by a computer using any suitable operating system. In an exemplary embodiment of the invention, one or more tasks according to exemplary embodiments of method and/or system as described herein are performed by a data processor, such as a computing platform for executing a plurality of instructions. Optionally, the data processor includes a volatile memory for storing instructions and/or data and/or a non-volatile storage, for example, a magnetic hard-disk and/or removable media, for storing instructions and/or data. Optionally, a network connection is provided as well. A display and/or a user input device such as a keyboard or mouse are optionally provided as well.

BRIEF DESCRIPTION OF THE DRAWINGS

Some embodiments of the invention are herein described, by way of example only, with reference to the accompanying drawings. With specific reference now to the drawings in detail, it is stressed that the particulars shown are by way of example and for purposes of illustrative discussion of embodiments of the invention. In this regard, the description taken with the drawings makes apparent to those skilled in the art how embodiments of the invention may be practiced.

In the drawings:

FIG. 4 schematically illustrates an exemplary disposable cap including a pressure sensing cover, according to some embodiments of the present invention;

FIG. 5 schematically illustrates an exemplary disposable cap including an ostomy bag housed in a bag cavity formed in a capsule between a proximal opening and a cover, according to some embodiments of the present invention;

FIG. 6 schematically illustrates an exemplary disposable cap including capsule covered by a removable film lid, according to some embodiments of the present invention;

FIGS. 13A-13C schematically illustrate an exemplary ostomy port including an attachment mechanism for attaching an elastic collection bag, according to some embodiments of the present invention;

FIGS. 14A-14D schematically illustrate an ostomy port including an attachment mechanism for attaching a collection bag used in domestic applications (for example, a sandwich bag, small garbage bags, and the like) to a proximal end of an elastic tube, according to some embodiments of the present invention;

DESCRIPTION OF SPECIFIC EMBODIMENTS OF THE INVENTION

Figure 1A:
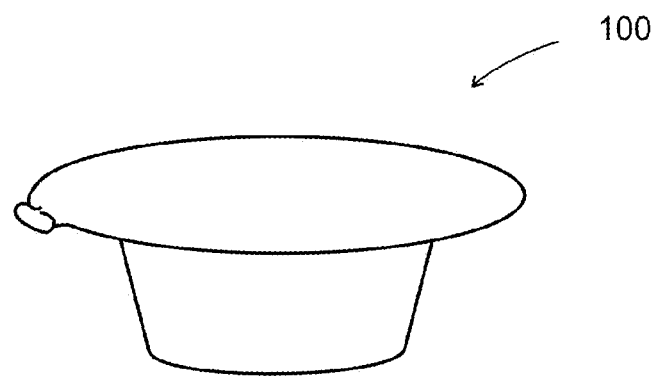
FIGS. 1A and 1B schematically illustrate a perspective view of an exemplary disposable cap and an exploded perspective view of the cap, respectively, according to an embodiment of the present invention.

The present invention, in some embodiments thereof, relates to ostomy ports and, more particularly, but not exclusively, to a disposable ostomy cap for use with ostomy ports and/or other parts, such as an ostomy bag or a whole port.

Reference hereinafter to an ostomy port or a stomal cover may include any of the embodiments described in any one of the applications from which this disclosure is claiming benefit and referenced in the above section Related Application.

An aspect of some embodiments of the present invention relates to a disposable cap for sealing a proximal opening of an ostomy port. The cap includes an ostomy bag which is deployable for collecting waste content flowing through the ostomy port and out the proximal opening.

As used hereinafter, distal refers to a direction away from the proximal opening and towards an interior of the abdominal cavity while proximal refers to a direction away from the abdominal cavity towards the proximal opening.

In some exemplary embodiments, the ostomy bag includes a collection volume for waste content in a range of 200-1000 ml, for example, 400 ml, 500 ml, 600 ml, 700 ml. Optionally, for irrigation purposes, the ostomy bag includes a volume ranging from 1000-1500 ml, for example, 1100 ml, 1250 ml, 1350 ml, 1450 ml. Additionally, a film thickness of the ostomy bag ranges between 50-200 μm, for example, 60 μm, 80 μm, 100 μm, 120 μm.

In some exemplary embodiments, the cap acts as a capsule for housing the bag. Optionally, the cap may include a coupling section for coupling to the ostomy port (may be referred to hereinafter also as a "coupler)". The capsule material may include plastic, hardened rubber, and/or any other waste content resistant material suitable for housing the bag and for being inserted into a proximal opening. An internal cavity in the capsule accommodating the bag may, for example, have a volume ranging between 3000-15000 $mm^3$, for example, 5000 $mm^3$, 6000 $mm^3$, 7000 $mm^3$ Optionally, the edge of an opening to the bag is adhered to the capsule by welding. Alternatively, the bag is adhered to the capsule by bonding or by any other method known in the art and suitable for adhering the bag material with the capsule material. Optionally, the capsule is conically shaped for providing for a greater volume of space into which the bag may be folded or furled due to an increasing cross-sectional area in the capsule in the proximal direction. Additionally or alternatively, the conical capsule allows for easier insertion of the cap into the proximal opening. This may reduce bulging of the cap in the proximal direction, making it less noticeable to the user or other people and/or easier for insertion into the proximal opening of an ostomy port. Additionally or alternatively, the conical capsule reduces the possibility of the bag bulging out in a distal direction from a distal opening of the capsule when furled inside the capsule. Optionally, the proximal end in the ostomy port is conically shaped for accommodating the cap.

In some exemplary embodiments, the cap includes a plastic cap cover. Alternatively, the cap does not have a cover on either a proximal end or a distal end. A user wishing to discharge waste content into the ostomy bag removes the cover and pulls out the bag. Alternatively, the cap cover includes an elastomeric material. Alternatively, the cap cover includes a flexible film. Alternatively, the cover is a lid which may be removed by stripping or peeling off the cap. Alternatively, the cap cover includes any other material suitable to cover a proximal opening in the capsule housing the folded and/or furled bag. Alternatively, the bag is held in an internal cavity of the capsule by a friction force, and may be manually pulled out by a user. Alternatively, the bag is held in an internal cavity of the capsule by a mechanical fixation element (e.g. an R-clip) that may be manually pulled out by a user.

In some exemplary embodiments, the cap is attached to the ostomy port using a twist-and-lock mechanism. Alternatively, the attachment includes a snap-lock mechanism. Alternatively, the attachment includes threading the cap into the proximal opening of the ostomy port. Alternatively, the cap may be integral to the ostomy port or to an insert to the port. Alternatively, other methods known in the art suitable for fastening the cap to the proximal opening may be used.

In some exemplary embodiments, the cap includes a sensing mechanism for communicating to the user of a need for evacuation by sensing an increase in intestinal pressure. Optionally, the cap includes a cover equipped with a flexible portion adapted to protrude (bulge) outwards in the proximal direction when exposed to axial pressure exerted by waste content or flatus. Alternatively, the bag may additionally serve as the cover. The protrusion distance in response to an axial pressure of 50 mmHg may range from 2-30 mm, for example, 3 mm, 5 mm, 7 mm, and 10 mm. Optionally, the flexible portion is concave shaped. In some embodiments, the material of the sensing cover may be an elastomer such as, for example, silicone rubber, and may be of a durometer ranging between 5-10 Shore A, for example, 40 shore A, 60 shore A, 70 shore A, 75 shore A. A thickness may range between 0.2-2 mm, for example 0.75 mm, 1 mm, 1.25 mm.

In some exemplary embodiments, the sensing mechanism includes logic implemented in the port for sensing the increase in intestinal pressure. Alternatively, the logic is implemented in the cap. Optionally, upon reaching a predetermined value, a visual and/or audible and/or sensible warning is generated for notifying the user of the increase pressure. The indication may be a mechanically activated protruding element which may be seen by the user, or an electrical or electromechanical indication such as, for example, a light, a vibration, a sound and/or a wireless signal (e.g., Bluetooth).

In some exemplary embodiments, the port includes a safety mechanism for releasing gas and/or waste content. The safety mechanism may eject the cover or a section of the cap when the axial pressure reaches the predetermined value. Optionally, the safety mechanism includes a pressure-sensitive mechanism. Additionally or alternatively, the safety mechanism includes logic circuitry and/or mechanical logic for determining when to release the cover. Optionally, the safety mechanism includes electro-mechanical components. Optionally, the bag is pushed out of the capsule by an axial pressure ranging between 50 mmHg-100 mmHg, for example, 65 mmHg, 75 mmHg, 90 mmHg, 95 mmHg. Once the waste content has been expelled or the colonic pressure has decreased below the predetermined value, the cover may be replaced onto the cap. Optionally, to exclude false alarms due to temporary colonic pressure pulses, the cover is released when a colonic pressure inside the ostomy port is equal to or greater than, for example, 60 mmHg for a period of time greater than 5 seconds, greater than 15 seconds, greater than 30 seconds, greater than 60 seconds, greater than 90 seconds. Optionally, the cover is released when the colonic pressure is greater than or equal to 80 mmHg, greater than or equal to 100 mmHg, greater than or equal to 150 mmHg, greater than or equal to 200 mmHg.

In some exemplary embodiments, a pressure sensor (not shown) is assembled in an interior of the ostomy port, for example on an internal wall of the ostomy port, and a control unit is assembled at a portion of the ostomy port externally to the user's body, for example on the stomal cover. The control unit receives pressure signals from said pressure sensor, and is programmed with a logic algorithm for selectively opening a gas release valve upon fulfillment of predetermined conditions, for example any of the following conditions:
 a. Internal pressure is greater than 60 mmHg for more than 1 min;
 b. Internal pressure is greater than 100 mmHg for more than 10 sec;
 c. Internal pressure is greater than 150 mmHg, immediate release.

Optionally, the ostomy port is equipped with an indication mechanism, for example visual, audible or vibrational alarm, to notify the user of an activation of the gas release valve. Additionally or alternatively, the control unit notifies the user on a need to release gas without automatically activating the gas release valve. Optionally, the gas release valve can be closed either manually by the user or automatically by said control unit when the internal pressure decreases, for example, to no greater than 30 mmHg.

In some exemplary embodiments, a pressure sensor and a control unit as those described above control the opening of a gas release valve and/or deploying of a disposable collection bag, according to a predetermined logic, for example:
 a. As internal pressure is greater than 60 mmHg for more than 1 min, open the gas release valve;
 b. As internal pressure is greater than 60 mmHg for more than 2 min, deploy the disposable collection bag;
 c. As internal pressure is greater than 100 mmHg for more than 10 sec, open the gas release valve;
 d. As internal pressure is greater than 100 mmHg for more than 30 sec, deploy the disposable collection bag;
 e. As internal pressure is greater than 150 mmHg, open the gas release valve immediately;
 f. As internal pressure is greater than 150 mmHg, deploy the disposable collection bag immediately;

Optionally, an alert may be sent over wireless to the user warning of a high pressure condition, for example, through Bluetooth to a receiver carried or worn by the user. Optionally, the user may be able to program the control for setting pressure levels and duration, type of alarm to activate and duration of the alarm, among other possible control features. The user may additionally control activation of a blocking element inside the port such as, for example, a balloon, a gas release valve, and the like.

In some exemplary embodiments, the cap includes a discharge content indicator and/or a safety release valve in case of excessive waste content inside the ostomy port. Additionally or alternatively, the cap includes a gas filter for filtering gas, including flatus, from inside the ostomy port and for releasing to the ambient.

In some exemplary embodiments, the ostomy bag is unfurled by the pushing of the waste content. Optionally, a portion of the bag is left unfurled for pulling by the user. Additionally or alternatively, a strap or cord is attached to the bag, either at a proximal or distal end, for the user to pull on for unfurling the bag.

In some exemplary embodiments, the ostomy bag includes a strand for closing the bag prior to disposal. Optionally, the strand is adapted to tie the bag along an upper portion of the bag. Optionally, the bag may be closed by a cap for sealing the opening to the bag. Additionally or alternatively, the cap is placed on the upper portion of the bag. Optionally, the bag is closed by means of a clasp, a string, a tie, or any other means known in the art for closing the bag.

In some exemplary embodiments, the ostomy bag is open ended for allowing flushing of the waste content inside the bag. A sleeve may be connected to the open end for directing the waste content into a toilet. Flushing may be performed while the cap is removed from the proximal opening of an ostomy port. Additionally or alternatively, flushing may be performed while the cap is connected to the proximal opening by injecting water through an irrigation port on the ostomy port. Optionally, the bag is reusable by closing the open end of the bag and/or the sleeve.

In some exemplary embodiments, the ostomy bag is supported against the body of the user for reducing pressure on the internal abdominal wall and/or on the intestine due to the weight of a full or partially full bag pulling on the ostomy port. The use of a support may be suitable for applications involving an ileostomy or a urostomy where the ostomy bag is deployed at all times for continuously collecting waste content. Additionally or alternatively, the use of a support may be suitable for applications where accumulating of waste matter inside the intestine is undesirable and the ostomy bag is hence deployed at all times. Additionally or alternatively, the use of a support may be suitable for bowel irrigation purposes. A tab may be included on the bag, for example on a top section, for adhering the bag to the user's abdomen for providing weight support. The tab may apply a tensile force for retaining the bag as it grows heavier with the accumulation of waste content. Additionally or alternatively, a tab may be included in a bottom section of the bag for adhering to a body portion of the user for providing additional support. Additionally or alternatively, a belt may be used for securing the bag against the user's waist. Additionally or alternatively, the stomal cover may be adhered to the user's abdomen for supporting the bag.

An aspect of some embodiments of the present invention relates to a disposable ostomy port including one or more features in a single component. Optionally, the ostomy port is for a one-time use. This may allow for relatively inexpensive and simple production of the port. The ostomy port includes a tube which connects at a distal end to an intestinal portion and a retention balloon for retaining the tube in a stoma, the balloon and the tube produced together from a same material. The material may be an elastic and flexible material such as, for example, silicone rubber, and may be of a durometer ranging from 10-80 Shore A, for example, 20 Shore A, 30 Shore A, 40 Shore A. Optionally, the port is produced by attaching a free end of the balloon to an external surface of the tube during assembly. In some embodiments, the balloon may have an inflation volume ranging from 25-100 ml for colostomy, and from 15-50 ml for ileostomy. A wall thickness of the balloon may range from 0.2 mm-1.5 mm, for example, 0.3 mm, 0.5 mm, 0.8 mm. The tube may have an internal diameter ranging from 15-35 mm for colostomy and from 10-25 mm for ileostomy and urostomy. A wall thickness of the tube may range from 0.3 mm-2 mm, for example, 0.8 mm, 1 mm, 1.2 mm, 1.5 mm, 1.8 mm. A length of the tube varies with an abdominal wall thickness and may range from 1 cm-15 cm, depending on the degree of slenderness of the user.

In some exemplary embodiment, the port includes a stomal cover. Optionally, the port includes an inflation lumen distally connected to the balloon for introducing an inflation fluid into the balloon. The inflation lumen may have an internal diameter ranging from 0.5-3 mm, for example, 1.5 mm, 2 mm, 2.5 mm. Additionally, the inflation lumen is proximally connected to an inflation valve through which the inflation fluid is introduced into the lumen. Optionally, disposable ostomy port includes a gas filtering mechanism.

In some exemplary embodiments, the tube includes a sealed proximal end so that waste content flowing through the tube is retained inside the tube. Alternatively, an ostomy bag attached to the proximal end is formed as a single component with the port. Optionally, the bag is furled up inside the proximal opening of the tube and is deployed for collecting waste content flowing through the tube. The ostomy bag may include a collection volume for waste content in a range of 200-1000 ml, for example, 400 ml, 500 ml, 600 ml, 700 ml. Additionally, a bag wall thickness may range from 0.1 mm-1 mm, for example, 0.3 mm, 0.5 mm, 0.7 mm. Optionally, the ostomy bag is coated with a low permeability material for reducing its permeability, for example, parylene. Additionally or alternatively, a cover is attached to the proximal opening. The cover may be of a rigid material, a semi-rigid material, or a flexible material, and may include a thickness ranging from 0.5 mm-3 mm, for example, 1 mm, 2 mm, 2.5 mm. Optionally, the cover may be of plastic or a high durometer elastomer, for example at least 70 Shore A. Optionally, the cover is a disposable cap as previously described.

In some exemplary embodiments, an attachment element is formed as a single component together with the tube. Alternatively, the attachment element is formed as a separate component from the tube. The attachment element may serve for attaching the cover to the proximal opening. Additionally or alternatively, the attachment element may serve for attaching an ostomy bag to the proximal opening. The attachment element may be disposable. Alternatively, the attachment element is reusable. The attachment mechanism may be of a rigid material or a semi-rigid plastic or a high durometer elastomer, for example at least 70 Shore A. The elastic collection bag may include a collection volume for waste content in a range of 200-1000 ml, for example, 400 ml, 500 ml, 600 ml, 700 ml.

In some exemplary embodiments, an elastic waste content bag is attachable to the proximal opening. The elastic waste content bag may include a stretchable elastomer such as, for example, silicone rubber or latex. The disposable ostomy port includes a rim over which an elastic opening of the bag is stretched, tightedly fitting the bag onto the port. Optionally, the port includes a locking mechanism for securing the elastic opening onto the rim. The locking mechanism may be of a rigid material or a semi-rigid plastic or a high durometer elastomer, for example at least 70 Shore A. The elastic collection bag may include a collection volume for waste content in a range of 200-1000 ml, for example, 400 ml, 500 ml, 600 ml, 700 ml.

In some exemplary embodiments, the port is adapted to be fitted with a domestic bag for use as a waste content bag (ostomy bag), for example, a sandwich bag, a small garbage bag, and the like. The port includes a rim around the proximal opening onto which the edge of the bag's opening is fitted. A securing element and a latching element are coupled onto the rim and over the edges of the bag's opening for securing the bag. The securing element and the latching element may be of a rigid material or a semi-rigid plastic or a high durometer elastomer, for example at least 70 Shore A. The securing element and the latching element may be configured for holding a bag of thickness of 50 μm with a pulling force of for example up to 1 kg, when engaged onto one another.

Figure 1B:
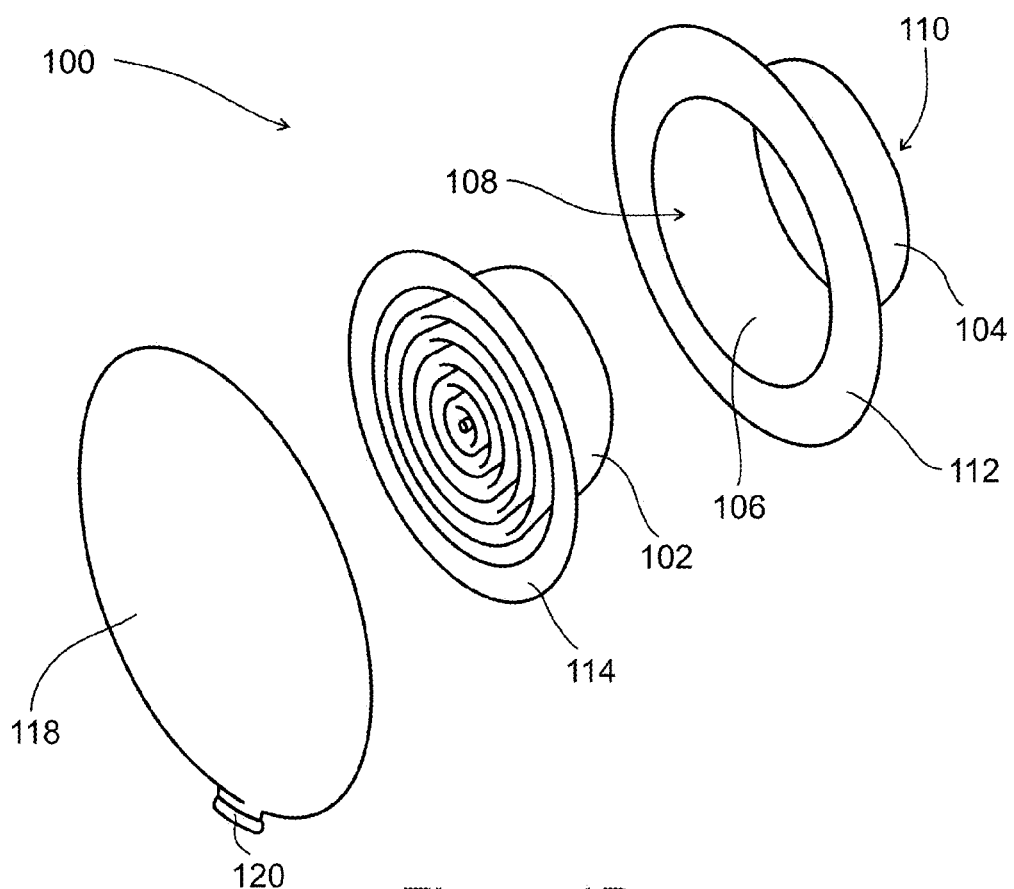
Figure 2:
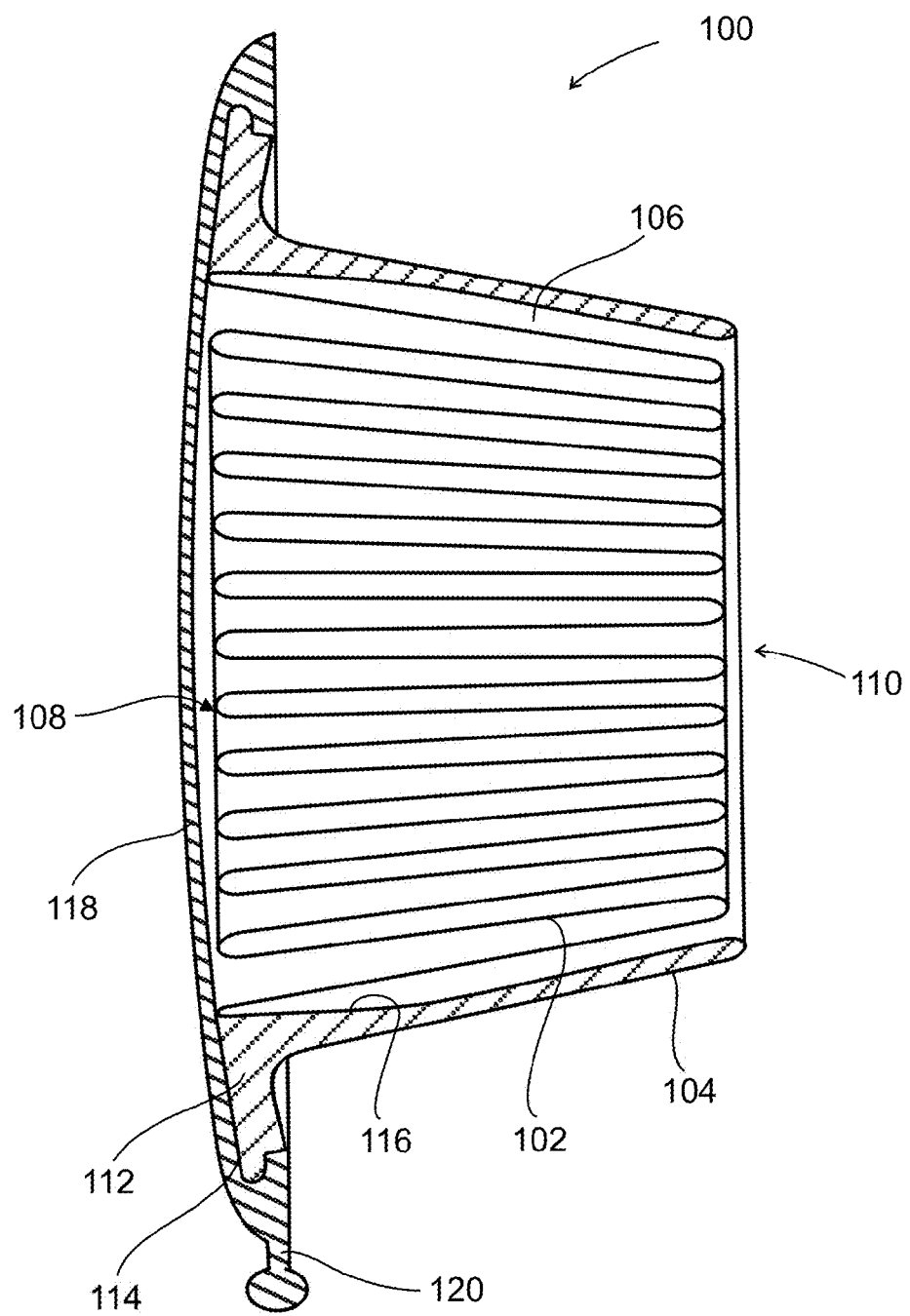
FIG. 2 schematically illustrates a sectional view of the cap, according to an embodiment of the present invention.

Reference is now made to FIGS. 1A and 1B which schematically illustrate a perspective view of an exemplary disposable cap 100 and an exploded perspective view of the cap, respectively, according to an embodiment of the present invention. Reference is also made to FIG. 2 which schematically illustrates a sectional view of cap 100, according to an embodiment of the present invention. Disposable cap 100 includes an ostomy bag 102 and a capsule 104 having an interior cavity 106 for housing the bag.

Capsule 104 includes a proximal opening 108 through which bag 102 is optionally inserted into cavity 106 during assembly of cap 100, and through which the bag is deployed for collecting waste content from an ostomy port. Optionally, bag 102 is folded inside cavity 106.

Capsule 104 additionally includes a distal opening 110 which fits through, or onto, a proximal opening of an ostomy port, and through which waste content flows from the port into bag 102. Optionally, capsule 104 is conically shaped with proximal opening 108 having a larger cross sectional area than distal opening 110. Alternatively, capsule 104 is cylindrically shaped. A rim 112 peripherally bounds proximal opening 108 and is an attachment surface for adhering an edge 114 to an opening into ostomy bag 102. Alternatively, edge 114 is adhered to an inner wall 116 of cavity 106.

Cap 100 includes a cover 118 for sealing proximal opening 108 with bag 102 inside cavity 106. Sealing of proximal opening 108 substantially prevents leakage of waste content through cap 100. Optionally, cover 118 includes a tab 120 for allowing a user to pull the cover off capsule 104. Optionally, cover 118 is non-replaceable and cannot be fitted onto capsule 104 following removal. Alternatively, cover 118 is replaceable. Cover 118 may be fitted onto capsule 104 using a snap-lock fastening mechanism, a twist-and-lock fastening mechanism, or any other type of mechanism known in the art and suitable for preventing leakage of waste content from proximal opening 108.

Figure 3A:
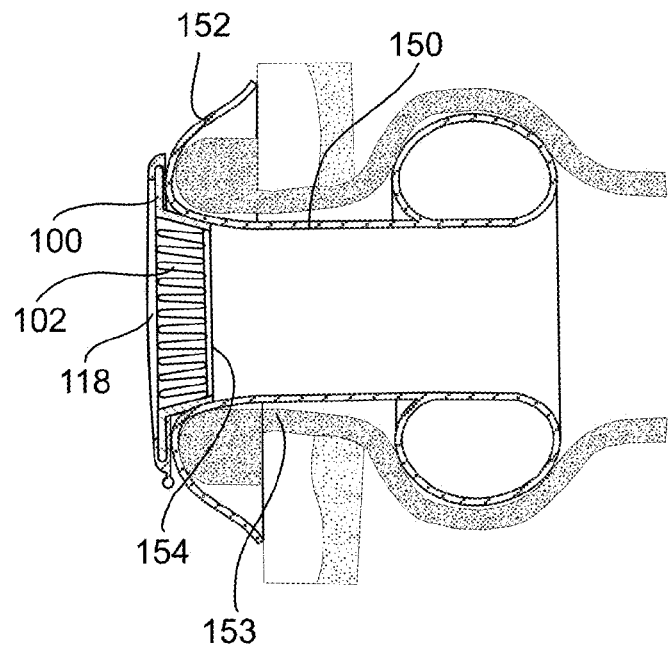
FIGS. 3A and 3B schematically illustrate the cap attached to an ostomy port having a stomal cover, in a waste continence mode and in a waste collection mode, respectively, according to some embodiments of the present invention.
Figure 3B:
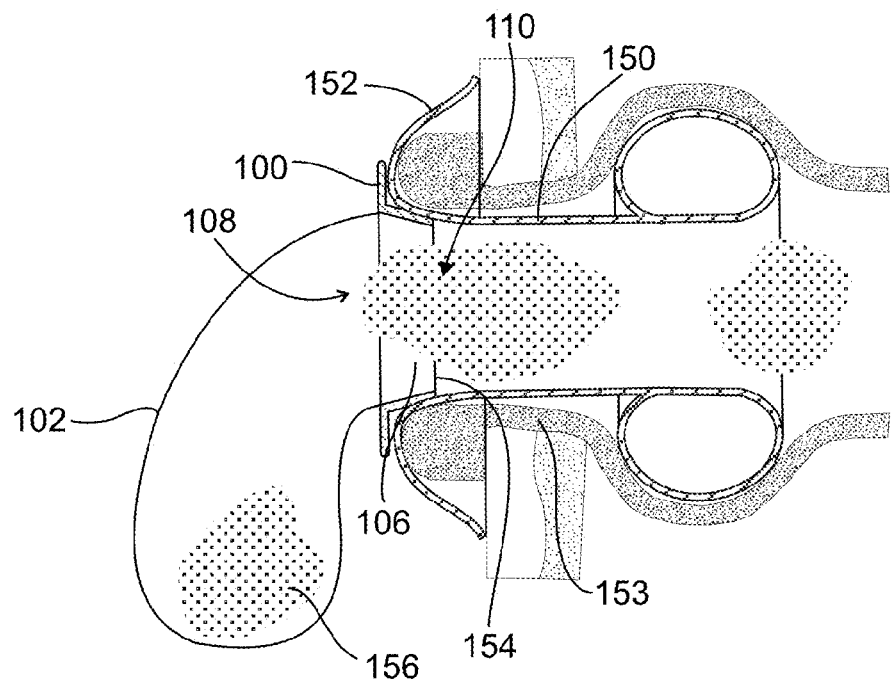

Reference is now made to FIGS. 3A and 3B which schematically illustrate cap 100 attached to an ostomy port 150 having a stomal cover 152, in a waste continence mode and in a waste collection mode, respectively, according to some embodiments of the present invention. Ostomy port 150 is inserted in a stoma 153.

In the waste continence mode, cap 100 is inserted into a proximal opening 154 in ostomy port 150, sealing against possible leakage of waste content from the ostomy port through the opening. Optionally, cap 100 is attached to stomal cover 152 by a snap-lock mechanism. Alternatively, other fastening mechanisms may be used, for example, a twist-and-lock mechanism, threaded fasteners, or other mechanism known in the art suitable for fastening cap 100 to ostomy port 150 while preventing leakage from proximal opening 154.

In the waste collection mode, bag 102 is deployed through proximal opening 108 in cap 100. Waste content 156 flows from ostomy port 150 through distal opening 110 in cap 100 into cavity 106 and therefrom through proximal opening 108 into bag 102. Optionally, the user removed cover 118 and pulled bag 102 through proximal opening 108 for deploying the bag. Alternatively, bag 102 is pushed out by axial pressure exerted on the bag by waste content 156. Additionally or alternatively, cover 118 was automatically ejected by the pressure of bag 102 pushing on the cover and/or was released by a pressure sensing mechanism in cap 100.

Reference is now made to FIG. 4 which schematically illustrates an exemplary disposable cap 200 including a pressure sensing cover 218, according to some embodiments of the present invention. Cap 200 includes bag 102 inside cavity 106 of capsule 104.

Pressure sensing cover 218 is made of a stretchable, flexible material and sealingly fits onto capsule 104 over proximal opening 108. Pressure sensing cover 218 is adapted to protrude in a proximal direction when an axial pressure 202 is applied by waste content and/or flatus through distal opening 110 in the direction of proximal opening 108. Optionally, bag 102 is pushed in the proximal direction by axial pressure 202 and pushes on cover 218. Optionally, protruding cover 218 is indicative of a need for the user to evacuate and/or to release flatus. Optionally, the user removes cover 218 by pulling on a tab 220 for releasing bag 102. Additionally or alternatively, the user releases flatus using a gas release mechanism existing in the ostomy port.

Reference is now made to FIG. 5 which schematically illustrates an exemplary disposable cap 300 including an ostomy bag 302 housed in a bag cavity 306 formed in capsule 104 between proximal opening 108 and a cover 318, according to some embodiments of the present invention. Bag cavity 306 is externally located to cavity 106 and is dimensioned for accommodating ostomy bag 302 folded inside. Optionally, the user removes cover 318 by pulling on a tab 320 for releasing bag 102.

Reference is now made to FIG. 6 which schematically illustrates an exemplary disposable cap 400 including capsule 104 covered by a non-reusable film lid 418, according to some embodiments of the present invention. Film lid 418 may include a plastic or flexible metal. Additionally or alternatively, film lid 418 includes a flexible metal coated with a plastic material suitable for welding onto a surface of capsule 104 (e.g. polyethylene). Optionally, the user removes film lid 418 by pulling on a tab 420.

Figure 7B:
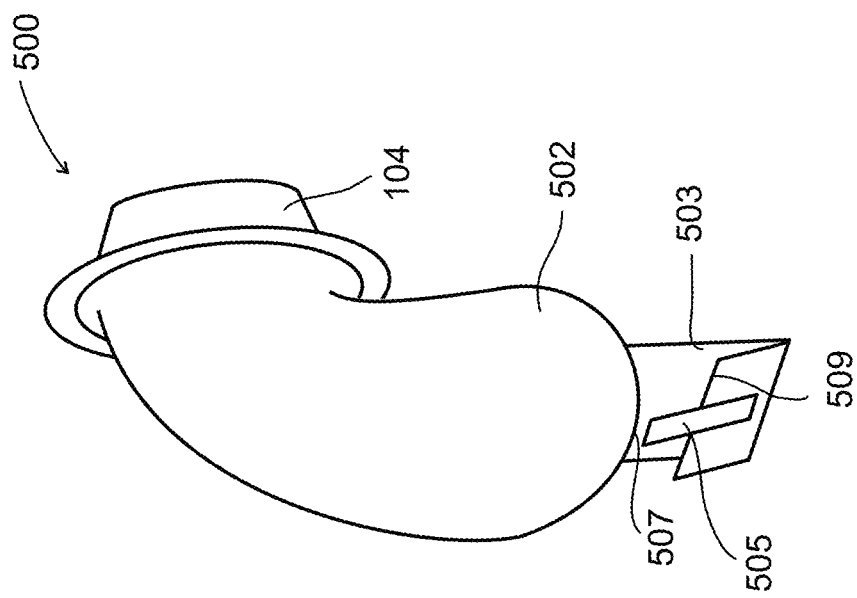
FIGS. 7A and 7B schematically illustrate an exemplary disposable cap including a reusable ostomy bag deployed from a capsule, according to some embodiments of the present invention.
Figure 7A:
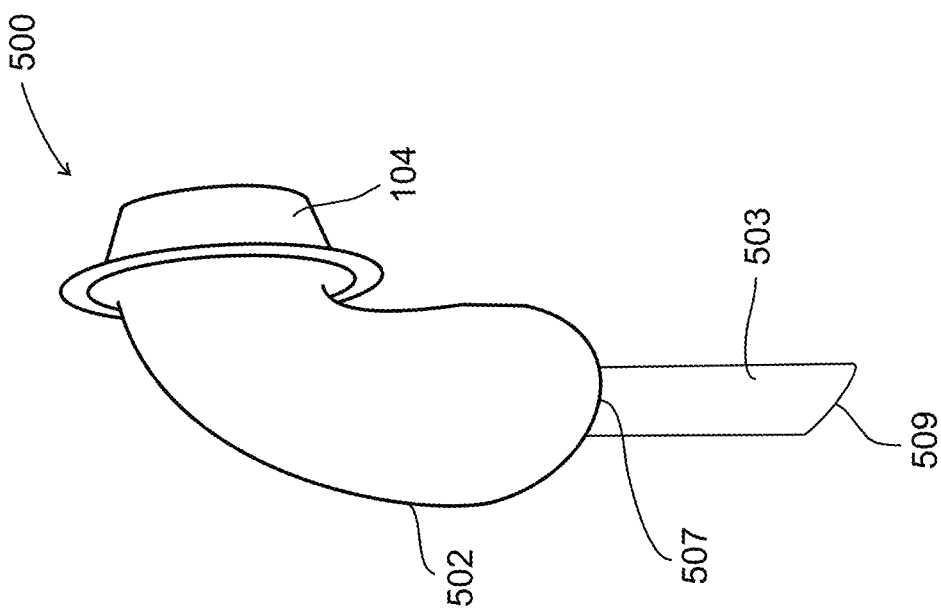

Reference is now made to FIGS. 7A and 7B which schematically illustrate an exemplary disposable cap 500 including a reusable ostomy bag 502 deployed from a capsule 104, according to some embodiments of the present invention. Bag 502 includes an opening 507 on a bottom portion of the bag connecting to a sleeve 503.

Sleeve 503 is used for flushing out waste content inside bag 502 for reusing the bag. Following evacuation, the user may approximate a sleeve opening 509 at the end of sleeve 503 to a toilet or other waste disposal means for discharging the waste content. Optionally, following discharge, the user may wash bag 502 including sleeve 503 for removing any remnants of waste content.

In FIG. 7A, cap 500 is shown removed from an ostomy port for discharging the waste content. Alternatively, waste content maybe discharged from bag 502 while cap 500 is attached to the ostomy port.

In FIG. 7B, bag 502 is shown with sleeve 503 closed for sealing opening 507 in bag 502 and sleeve opening 509. Optionally, sleeve 503 is closed when bag 502 is folded inside capsule 104. Additionally or alternatively, sleeve 503 is closed for reuse following flushing of the waste content. In the closed position, sleeve 503 is folded and/or furled for preventing leakage from the sleeve, and adhered to bag 502. Optionally, sleeve 503 is adhered to bag 502 using an adhesive strip 505. Alternatively, other fastening mechanisms may be used, for example, a hook-and-loop fastener.

Figure 8B:
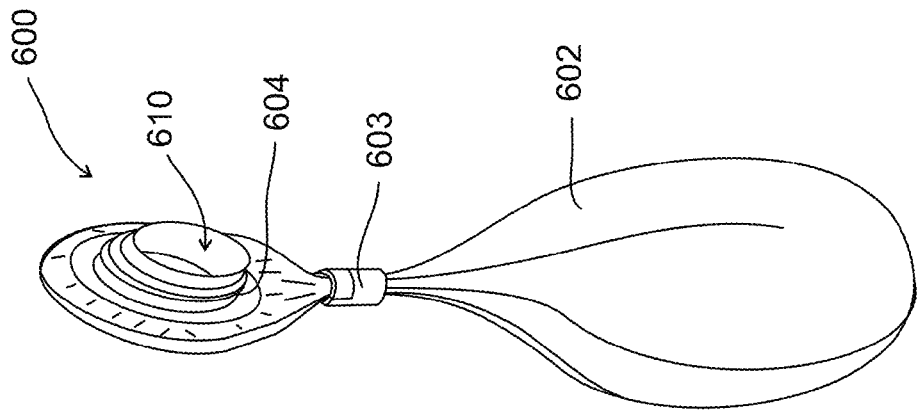
FIGS. 8A and 8B schematically illustrate a method of closing an exemplary ostomy bag in a disposable cap following collection of waste content from an ostomy port, according to some embodiments of the present invention.
Figure 8A:
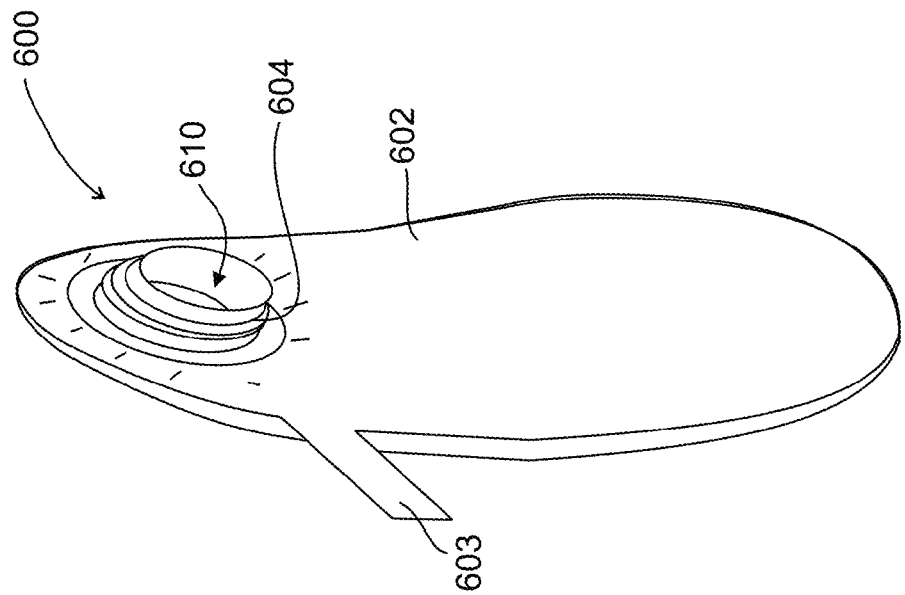

Reference is now made to FIGS. 8A and 8B which schematically illustrate a method of closing an exemplary ostomy bag 602 in a disposable cap 600 following collection of waste content from an ostomy port, according to some embodiments of the present invention. Waste collection bag 602 includes a strand 603 which is wrapped around a portion of the bag below capsule 604, closing (clamping) the bag and preventing waste content from reaching the capsule (and spill out distal opening 610). Alternatively, waste collection bag 602 may include other means of securing the bag below capsule 604 for preventing waste content from reaching the capsule. For example, bag 602 may be clasped below capsule 604 with a clip, or a tie wire, or any other suitable tie means. Optionally, the tie means may be reusable. Alternatively, the tie means are disposed of with bag 602. Alternatively, a cover may be fitted on distal opening 610 for sealing the opening and preventing waste content from leaking out bag 602.

Figure 9C:
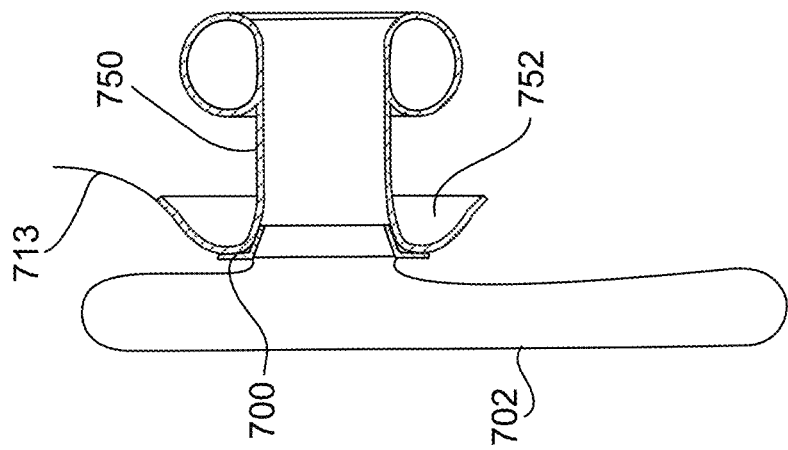
FIGS. 9A-9C schematically illustrate an exemplary disposable cap with a supported deployed ostomy bag, according to some embodiments of the present invention.
Figure 9B:
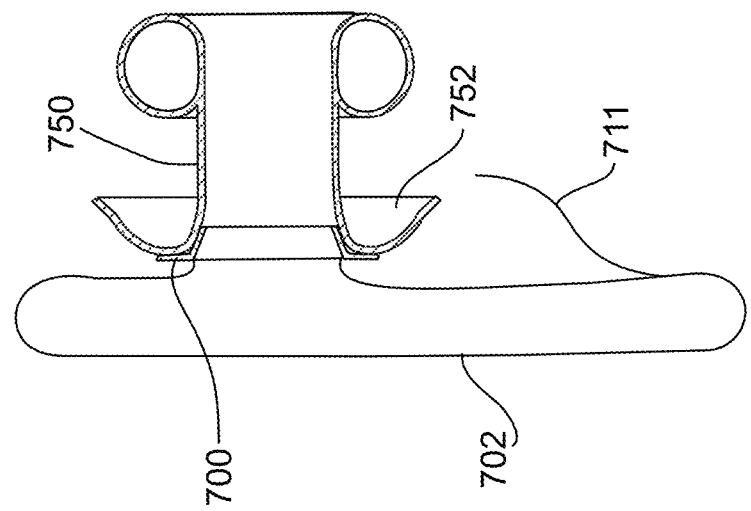
Figure 9A:
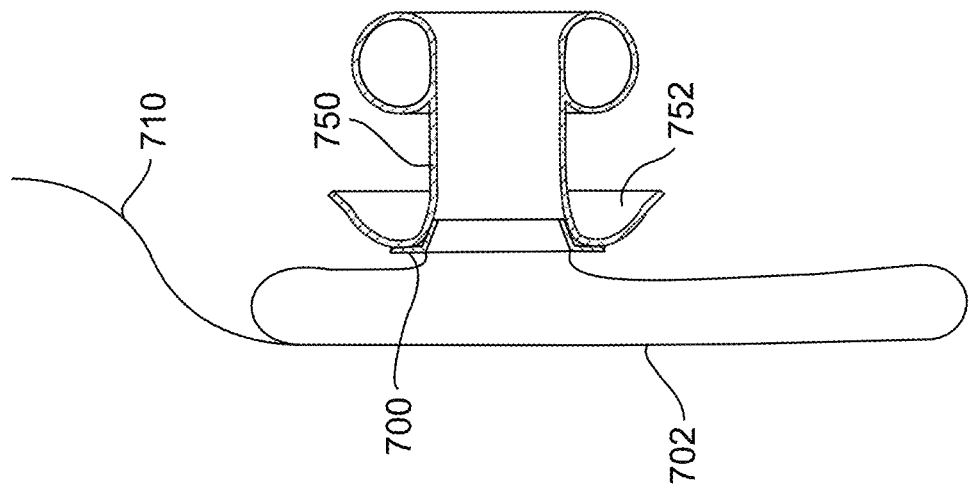

Reference is now made to FIGS. 9A to 9C which schematically illustrate an exemplary disposable cap 700 with a supported deployed ostomy bag 702, according to some embodiments of the present invention. Disposable cap 700 is attached to a stomal cover 752 in an ostomy port 750, bag 702 continuously deployed as may be typical for example for an ileostomy or a urostomy for collecting waste content continuously.

In FIG. 9A, a weight of a partially full, or full, ostomy bag 702 is supported by a tab 710 attached to an upper section of the bag and adhered to a body section of the user, for example, to an external abdominal wall. Optionally, tab 710 increases a tensile pulling force on bag 702 as the bag grows heavier with the weight of collected waste content. Additionally or alternatively, ostomy bag 702 is supported by a tab 711 attached to a bottom section of the bag, as shown in FIG. 9B. Additionally or alternatively, bag 702 is supported by adhering stomal cover 752 to the external abdominal wall of the user, optionally by a tab 713 attached to the stomal cover.

Figure 10:
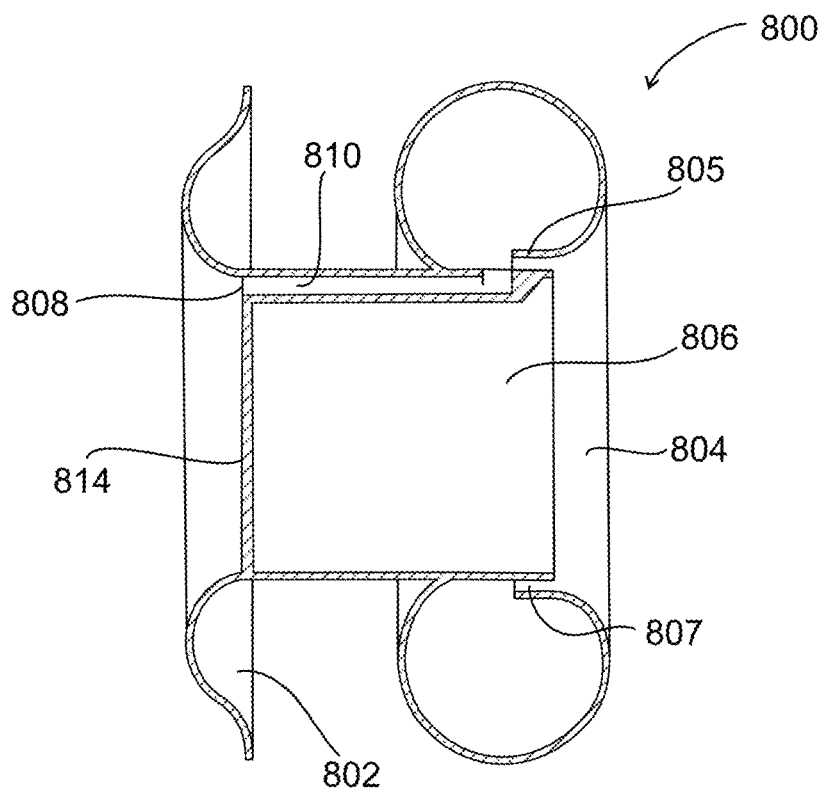
FIG. 10 schematically illustrates an exemplary ostomy port including an elastic stomal cover, an inflatable balloon, and an elastic tube all integrally formed as a single component suitable for one-time use, according to some embodiments of the present invention.

Reference is now made to FIG. 10 which schematically illustrates an exemplary ostomy port 800 including an elastic stomal cover 802, an inflatable balloon 804, and an elastic tube 806 all integrally formed as a single component suitable for one-time use, according to some embodiments of the present invention. Ostomy port 800 includes an inflation port 808 and an inflation lumen 810 through which balloon 804 is inflated with an inflation fluid. Optionally, balloon 804 is formed with a loose end 805 attachable to a distal exterior surface 807 of elastic tube 806 during manufacture of ostomy port 800. Optionally, a proximal end of elastic tube 806 is fitted with a non-removable cover 814 (or seal). Additionally, ostomy port 800 is removable from a stoma and disposed of when filled with waste content. Prior to removal, balloon 804 is deflated. Optionally, balloon 804 is deflated by removing the inflation fluid through inflation lumen 810 and inflation port 808.

Figure 11:
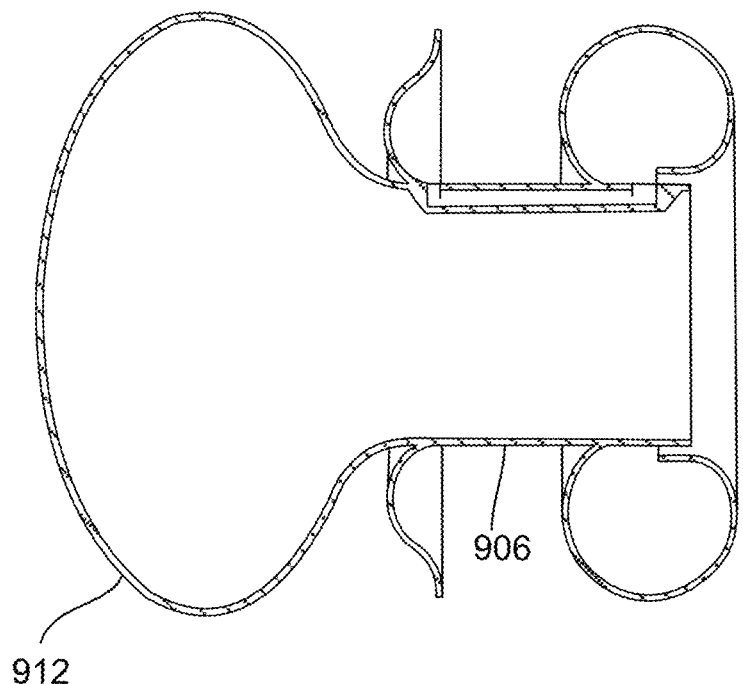
FIG. 11 schematically illustrates an exemplary ostomy port for a one-time use with a built-in ostomy bag for collecting waste content, according to some embodiments of the present invention.

Reference is now made to FIG. 11 which schematically illustrates an exemplary ostomy port 900 for a one-time use with a built-in ostomy bag 912 for collecting waste content and/or irrigation fluid, according to some embodiments of the present invention. Optionally, ostomy port 900 is formed as a single component similar to stomal insert 800 shown in FIG. 10 having ostomy bag 912 instead of cover 814.

Ostomy port 900 includes an elastic tube 906 to which ostomy bag 912 is attached at a proximal end. Optionally, ostomy bag 912 is furled inside elastic tube 906 prior to deployment. Optionally, ostomy bag 912 is deployed by a user pulling on the bag. Additionally or alternatively, ostomy bag 912 is deployed by an axial pressure of the waste content or flatus on the bag. Ostomy bag 912 may have any shape suitable for collecting waste content discharged through elastic tube 906. Alternatively, ostomy bag 912 is attached to an attachment mechanism (not shown) on elastic tube 906.

Figure 12:
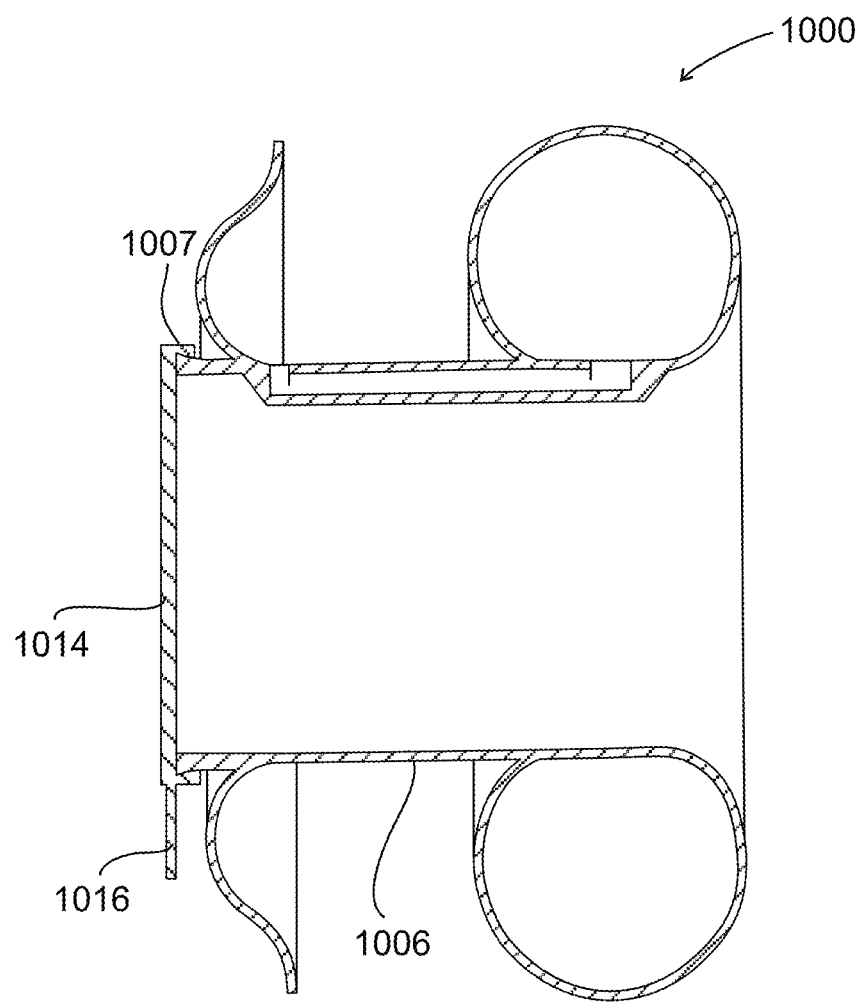
FIG. 12 schematically illustrates an ostomy port including a removable cap for removing waste content, according to some embodiments of the present invention.

Reference is made to FIG. 12 which schematically illustrates an ostomy port 1000 with a removable cap 1014 for removing waste content, according to some embodiments of the present invention. Optionally, ostomy port 1000 is formed as a single component similar to ostomy port 800 shown in FIG. 10, excluding removable cap 1014 which may be separately produced from the ostomy port.

Ostomy port 1000 includes an elastic tube 1006 with a cap attachment mechanism 1007 for securing cap 1014 to the port. Removable cap 1014, in some embodiments, has a tab 1016 for easy removal of the cap. Optionally, attachment mechanism 1007 is adapted to be fitted with a collection bag (not shown) into which waste content flows out of ostomy port 1000 following removal of cap 1014. Optionally, the collection bag is attached to attachment mechanism 1007 following removal of cap 1014. Optionally, cap 1014 is suitable for one-use, and is replaced with a new cap after it is being removed from ostomy port 1000. Alternatively, cap 1014 is reusable.

Reference is now made to FIGS. 13A-13C which schematically illustrate an exemplary ostomy port 1100 including an attachment mechanism 1107 for attaching an elastic collection bag 1112, according to some embodiments of the present invention. Optionally, ostomy port 1100 is formed as a single component similar to ostomy port 800 shown in FIG. 10.

Elastic collection bag 1112 includes an opening 1115 with an annular elastic rim 1113 adapted to be inserted in a circumferential recess 1114 in attachment mechanism 1107. Optionally, attachment mechanism 1107 includes locking mechanism 1111 for locking annular elastic rim 1113 inside circumferential recess 1114. Additionally, attachment mechanism 1107 is adapted to support a weight of collection bag 1112 when partially full, optionally full, with waste content. Optionally, annular elastic rim 1113 includes a latex material or other type of elastomeric material. Alternatively, annular elastic rim 1113 is non-elastic and is preformed of a circumference suitable for fitting in circumferential recess 1114 and locked in place by locking mechanism 1111.

Reference is now made to FIGS. 14A-14D which schematically illustrate an ostomy port 1200 including an attachment mechanism 1207 for attaching a collection bag 1212 used in domestic applications (for example, a sandwich bag, small garbage bags, and the like) to a proximal end of an elastic tube 1206, according to some embodiments of the present invention. Optionally, ostomy port 1200 is formed as a single component similar to ostomy port 800 shown in FIG. 10.

In some exemplary embodiments, attachment mechanism 1207 includes a snap-fitting arrangement for attaching a removable annular fastener 1213 having an opening 1211 through which a portion of collection bag is inserted. Optionally, annular fastener 1213 includes a latching element 1217 which snap-fits onto attachment mechanism 1207 and secures a rim portion 1219 of collection bag 1212 between the latching element and the attachment mechanism. Alternatively, other fastening arrangements known in the art may be used for removable annular fastener 1213 and attachment mechanism 1207, for securing collection bag 1212 to ostomy port 1200. These may include twist-locking and securing rim portion 1219 by pressing on the rim portion in an axial direction parallel to that of elastic tube 1206, or using a spring mechanism in attachment mechanism 1207 so that the spring secures the rim portion while pressing against annular fastener 1213.

Figure 15:
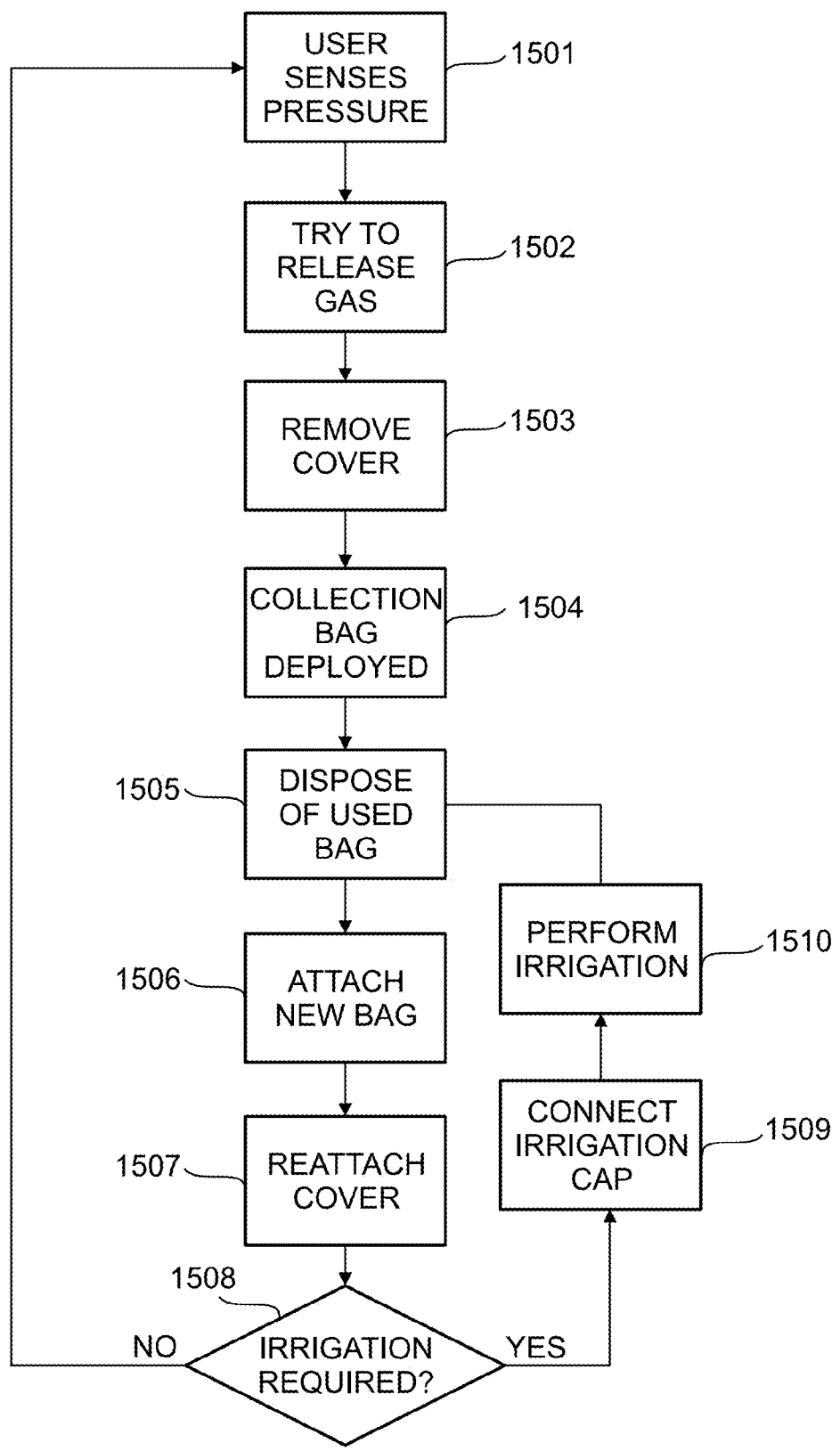
FIG. 15 illustrates a flow chart of a method for using a disposable cap with an ostomy port, according to an embodiment of the present invention.

Reference is now made to FIG. 15 which illustrates a flow chart of a method for using a disposable cap with an ostomy port, according to an embodiment of the present invention. The method illustrated and described herein is not intended to be limiting in any way, and an ordinary person skilled in the art may find that there are numerous other ways of implementing the method.

At 1501, the user, during the course of the day, senses pressure from waste content which requires evacuation. Optionally, the pressure is sensed through a sensing cover attached to the cap protruding in a proximal direction. Alternatively, the pressure is electrically sensed by logic in the cap. Alternatively, the pressure is mechanically sensed by mechanical sensing components in the cap. Optionally, a visual and/or audio and/or sensible warning is provided to the user.

At 1502, optionally, in response to the sensed pressure the user activates a gas release mechanism for releasing flatus, and then returns to stage 1501.

At 1503, the user removes the cover. Alternatively, the cover is ejected by the safety mechanism.

At 1504 the ostomy bag is automatically deployed by the axial pressure from the waste content pushing on the bag, allowing the waste content to flow into the bag. Alternatively, the user deploys the bag using a strap or cord that is attached to the bag, or any other method suitable for deployment of the bag.

At 1505, the user having finished evacuation replaces the disposable ostomy bag which includes the waste content. The user releases the disposable cap from the ostomy port for replacement. The user may wipe the ostomy port with a tissue or other suitable material for removing possible residues inside port. The user then discards the used ostomy bag with the attached capsule. Optionally, the sensing cover is discarded with the capsule. Alternatively, the cover is kept for use with the replacing bag and capsule.

Optionally at 1506, the user attaches a new cap including a new folded bag to the ostomy port.

Optionally at 1507, the user attaches a sensing cover to the cap. Optionally, the sensing cover is that previously used. Alternatively, the cap in 1506 includes the sensing cover.

Optionally at 1508, the user, during the course of the day, may require irrigation. If irrigation is required continue to 1509. If irrigation is not required, go to 1501.

Optionally at 1509, the user detaches the regular cap and attaches a dedicated cap for irrigation. This cap may have a collection bag with higher volume, and/or supports the weight of the bag.

Optionally at 1510, the user connects an irrigation fluid source to the ostomy port. The user removes the cover deploying the bag and opens an irrigation valve in the ostomy port. Irrigation fluid flows through the port washing out the intestine and the port. The washed out waste content flows into the bag. Optionally, the user may introduce the irrigation fluid and allow the fluid to remain inside the bowel for some time, and only then remove the cover and deploy the bag to allow bowel content flush out. The user may wipe the ostomy port with a tissue or other suitable material (optionally pre-stored in the cap) for removing possible residues inside port. Once finished irrigating, optionally go to 1505.

Figure 16:
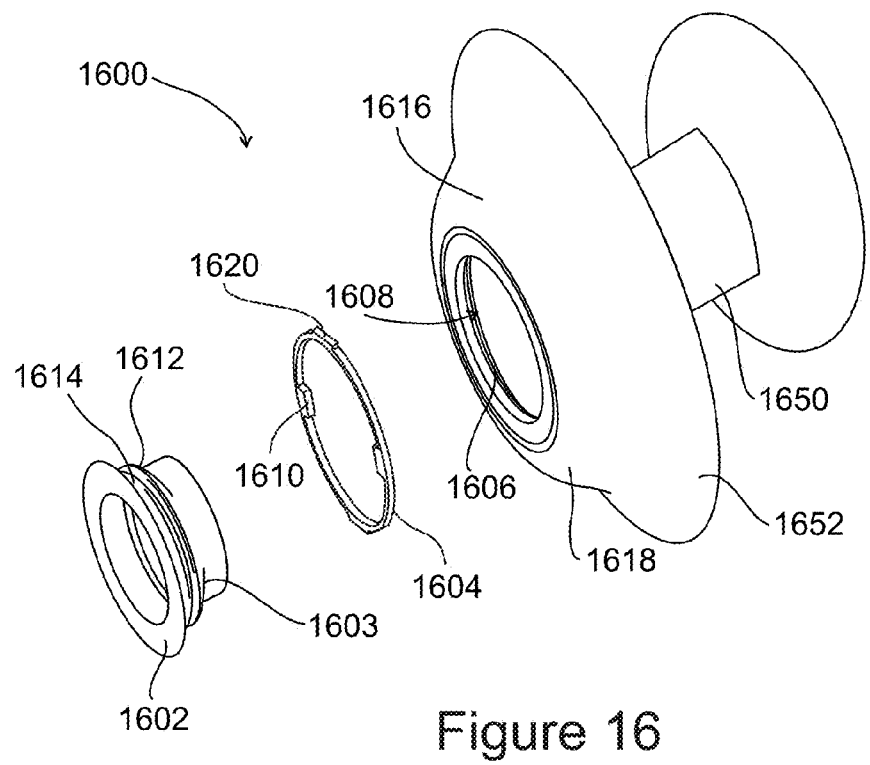
FIG. 16 schematically illustrates an attachment mechanism for attaching a disposable cap with an ostomy bag inside a capsule into an ostomy port, according to some embodiments of the present invention.

Reference is now made to FIG. 16 which schematically illustrates an attachment mechanism 1600 for attaching a disposable cap 1602 with an ostomy bag inside a capsule 1603 into an ostomy port 1650, according to some embodiments of the present invention.

An elastic ring 1604 having an oval shape is inserted (during assembly of the device at the factory) into a corresponding recess 1606 in the proximal opening of ostomy port 1650. In order to attach cap 1602, the user pushes the cap into proximal opening 1608. Tabs 1610 in elastic ring 1604 are pushed apart from each other by an inclined surface 1612 in capsule 1603. When cap 1602 is fitted into proximal opening 1608, ring 1604 assumes its original shape and tabs 1610 fit into circumferential recess 1614 in capsule 1603. For releasing capsule 1603, the user presses on a top side 1616 and a bottom side 1618 of stomal cover 1652, pressing opposing surfaces 1620 on ring 1604. Tabs 1610 are pushed apart from each other and capsule 1603 is released.

Figure 17:
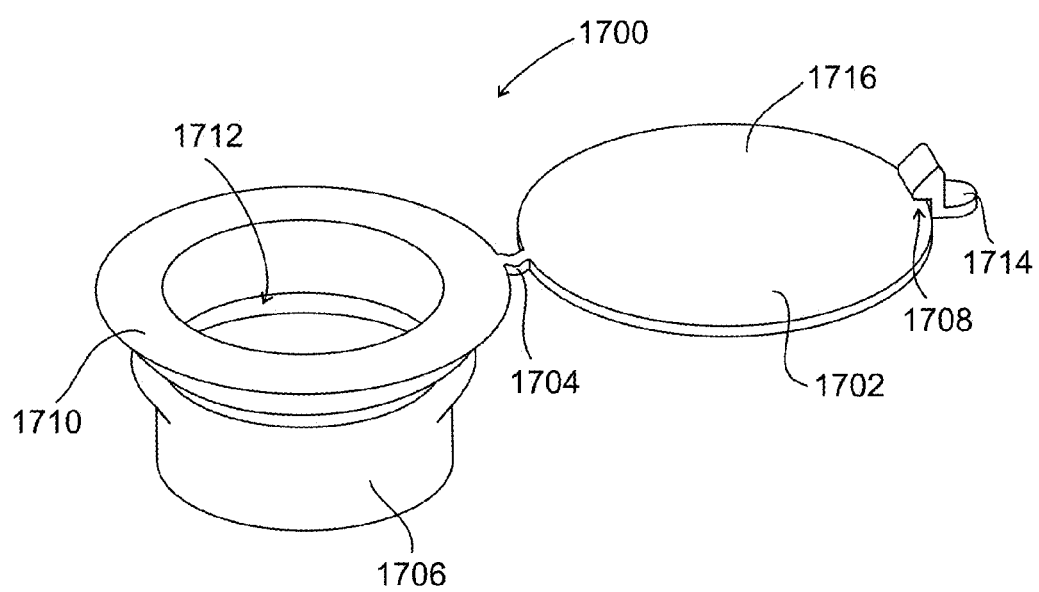
FIG. 17 schematically illustrates a quick release mechanism for removing a cover from a disposable cap for use with an ostomy port, according to some embodiments of the present invention.

Reference is now made to FIG. 17 which schematically illustrates a quick release mechanism for removing a cover 1702 from a disposable cap 1700 for use with an ostomy port, according to some embodiments of the present invention.

Cover 1702 is formed as one component with a capsule 1706, joined together by a strip 1704 which serves as a hinge. During assembly of cap 1700, the assembler flips cover 1702 such that a recess 1708 locks onto a circumferential rim 1710 in capsule 1706. Optionally, to release cover 1702 and deploy the ostomy bag inside cavity 1712, the user presses a tab 1714 in the proximal direction to release recess 1708 from circumferential rim 1710. Optionally, a portion of the bag (not shown) is attached (for example by bonding or welding) to an inner surface 1716 of cover 1702, such that when the cover is opened the bag is pulled out of capsule 1706.

Figure 18C:
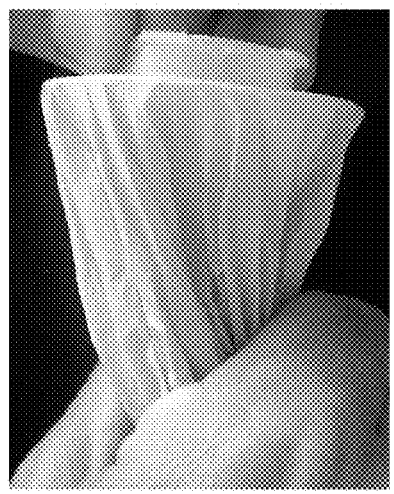
FIGS. 18A-18H illustrate an exemplary method of furling an ostomy bag into a disposable cap and placing a cover on the cap, according to some embodiments of the present invention.
Figure 18B:
Figure 18A:
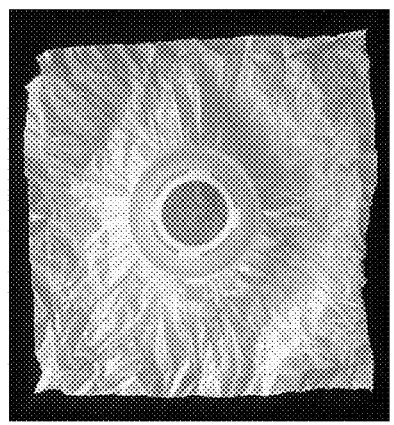
Figure 18F:
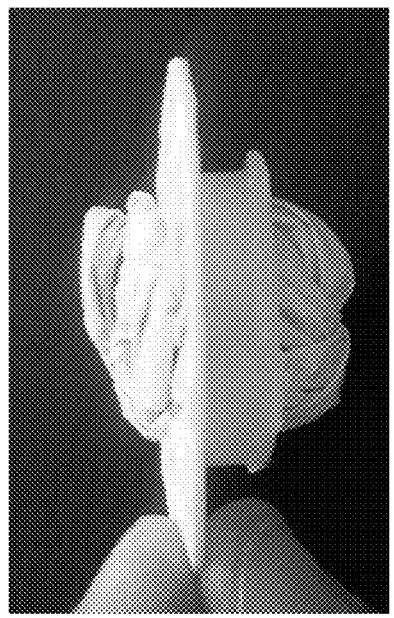
Figure 18E:
Figure 18D:
Figure 18H:
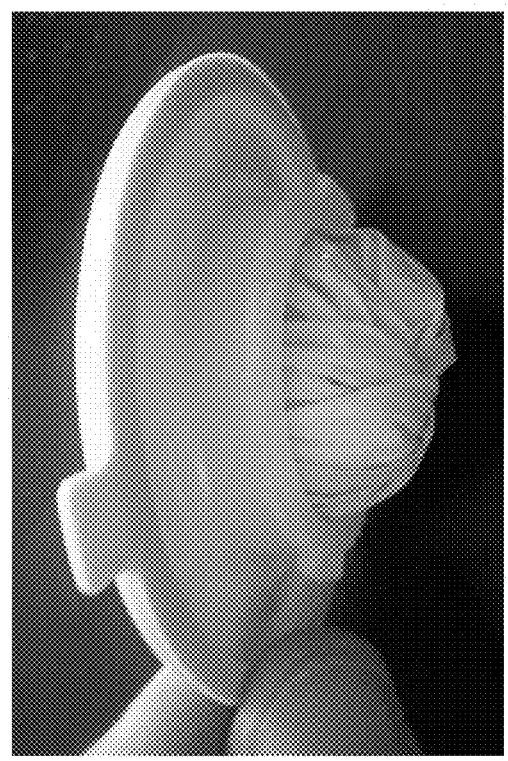
Figure 18G:
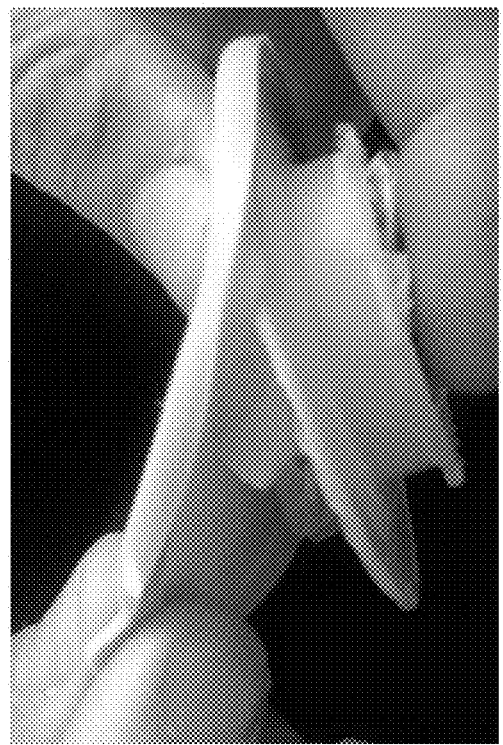

Reference is now made to FIGS. 18A to 18H which illustrate an exemplary method of furling an ostomy bag into a disposable cap and placing a cover on the cap, according to some embodiments of the present invention. FIG. 18A illustrates the collection bag and the capsule before furling process, as viewed from the distal direction. In FIG. 18B the assembler pulls a proximal portion of the collection bag apart and away from the capsule until it attains an elongated shape. In FIG. 18C the assembler grasps a proximal portion of the elongated collection bag within a fist. In FIG. 18D the assembler rotates said proximal portion around an axis of the capsule to 45 degrees in a clockwise direction. Alternatively, said proximal portion is rotated to 90 degrees. Alternatively, said proximal portion is rotated in the counterclockwise direction. In FIG. 18E, the assembler inserts said rotated proximal portion into an internal cavity of the capsule. FIG. 18F illustrates a distal view of the collection bag furled in the capsule. In FIG. 18G, the assembler places a cover on the cap, securing the furled collection bag inside the capsule. FIG. 18H illustrates the cap at the end of the assembly process.

The terms "comprises", "comprising", "includes", "including", "having" and their conjugates mean "including but not limited to".

The term "consisting of" means "including and limited to".

The term "consisting essentially of" means that the method or structure may include additional steps and/or parts, but only if the steps and/or parts do not materially alter the basic and novel characteristics of the claimed method or structure.

As used herein, the singular form "a", "an" and "the" include plural references unless the context clearly dictates otherwise.

Throughout this application, various embodiments of this invention may be presented in a range format. It should be understood that the description in range format is merely for convenience and brevity and should not be construed as an inflexible limitation on the scope of the invention. Accordingly, the description of a range should be considered to have specifically disclosed all the possible subranges as well as individual numerical values within that range. For example, description of a range such as from 1 to 6 should be considered to have specifically disclosed subranges such as from 1 to 3, from 1 to 4, from 1 to 5, from 2 to 4, from 2 to 6, from 3 to 6 etc., as well as individual numbers within that range, for example, 1, 2, 3, 4, 5, and 6. This applies regardless of the breadth of the range.

Whenever a numerical range is indicated herein, it is meant to include any cited numeral (fractional or integral) within the indicated range. The phrases "ranging/ranges between" a first indicate number and a second indicate number and "ranging/ranges from" a first indicate number "to" a second indicate number are used herein interchangeably and are meant to include the first and second indicated numbers and all the fractional and integral numerals therebetween.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable subcombination or as suitable in any other described embodiment of the invention. Certain features described in the context of various embodiments are not to be considered essential features of those embodiments, unless the embodiment is inoperative without those elements.

Although the invention has been described in conjunction with specific embodiments thereof, it is evident that many alternatives, modifications and variations will be apparent to those skilled in the art. Accordingly, it is intended to embrace all such alternatives, modifications and variations that fall within the spirit and broad scope of the appended claims.

All publications, patents and patent applications mentioned in this specification are herein incorporated in their entirety by reference into the specification, to the same extent as if each individual publication, patent or patent application was specifically and individually indicated to be incorporated herein by reference. In addition, citation or identification of any reference in this application shall not be construed as an admission that such reference is available as prior art to the present invention.

What is claimed is:

1. A cap for sealing a proximal opening in an ostomy port, including:
   a collapsed ostomy bag held within said cap;
   wherein said cap includes an automatic safety mechanism comprising a cover positioned over said collapsed ostomy bag by attachment to a proximal end of said cap, the cover in said attached position blocking bag expansion beyond a proximal end of said cap;
   said safety mechanism being configured for automatic release of said cover from said expansion-blocking position to a release configuration upon a predetermined pressure being exerted from within said cap;
   wherein said release of said cover to said release configuration comprises at least partial detachment of said cover from said cap, permitting deployment of said bag to expand beyond said cap end, such that said pressure is relieved; and
   said safety mechanism also being manually actuatable for manual release of said cover from said expansion-blocking position to said release configuration, permitting said deployment of said bag.

2. A cap according to claim 1, wherein the pressure is due to intestinal pressure.

3. A cap according to claim 1, further including a deployment prevention element.

4. A cap according to claim 1, wherein said bag is housed in a body of said cap.

5. A cap according to claim 1, wherein said bag is housed in a proximal portion of said cap.

6. A cap according to claim 1, wherein said cap is wider at a proximal side thereof than at a distal side thereof.

7. A cap according to claim 1, wherein said cap is configured to extend less than 1 cm proximally from said port.

8. A cap according to claim 1, wherein said cap is configured to fit into said port.

9. A cap according to claim 1, wherein said cap is configured to interlock with an interlocking mechanism of said port.

10. A cap according to claim 1, wherein said bag is configured to deploy when a pressure in said port is above a preselected threshold.

11. A cap according to claim 1, wherein said bag includes a pullable element for manual deployment.

12. A cap according to claim 1, wherein said cap includes a pressure indicator.

13. A cap according to claim 1, wherein said cap includes a sensing circuitry.

14. A cap according to claim 1, wherein said cap includes a foil seal.

15. A cap according to claim 1, wherein said cap includes a separately openable and closable cap-covering.

16. A cap according to claim 1, wherein said cap includes a separately openable cap-covering.

17. A cap according to claim 16, wherein said cap has a sleeve-shaped body and wherein said cap-covering is configured to fit on two opposite sides of said body.

18. A cap according to claim 1, comprising a removable cap-covering formed of an elastomeric material.

19. A cap according to claim 1 comprising a cap-covering, wherein said cap-covering is removable to allow deployment of said bag.

20. A cap according to claim 1, wherein said bag is integrally formed with said cap.

21. A cap according to claim 1, wherein said bag is permanently attached to said cap.

22. A cap according to claim 1, wherein said cap includes a closure for sealing said bag after filling thereof.

23. A cap according to claim 1, wherein said cap includes an adhesive attachment element for attaching said bag after deployment directly to a body of a patient.

24. A cap according to claim 1, wherein said bag has a volume when collapsed of less than 10 cc and when full of at least 300 cc.

25. A cap according to claim 1, wherein said safety mechanism is configured to eject a section of said cap when a pressure inside said cap reaches a predetermined value.

26. A cap according to claim 16, wherein said safety mechanism is configured to eject said cap-covering when a pressure inside said cap reaches a predetermined value.

27. A cap according to claim 1, wherein said safety mechanism includes a pressure-sensitive mechanism.

28. A cap according to claim 26, wherein said safety mechanism includes at least one of logic circuitry and mechanical logic configured for determining when to release said cap-covering.

29. A cap according to claim 1, wherein said safety mechanism includes electro-mechanical components.

30. A cap according to claim 1, wherein said safety mechanism is configured for pushing said bag out of said cap.

31. A cap according to claim 1, wherein said safety mechanism is configured for being actuated by a pressure ranging between 50 mmHg and 200 mmHg.

32. A cap according to claim 31, wherein said safety mechanism is configured for being actuated by a pressure of one of 65 mmHg, 75 mmHg, 80 mmHg, 90 mmHg, 95 mmHg, 100 mmHg, 150 mmHg, and 200 mmHg.

33. A cap according to claim 1, wherein said safety mechanism is configured for being actuated when a pressure inside said cap exceeds a predetermined value for a predetermined period of time.

34. A cap according to claim 33, wherein said predetermined pressure is one of 60 mmHg, 100 mmHg, and 150 mmHg.

35. A cap according to claim 33, wherein said predetermined period of time is greater than one of 5 seconds, 10 seconds, 15 seconds, 30 seconds, 60 seconds, and 90 seconds.

36. A cap according to claim 1, further comprising a pressure sensor and a control unit, said control unit configured to receive pressure signals from said pressure sensor, said control unit being programmed with a logic algorithm for performing predetermined actions upon fulfilling predetermined conditions.

37. A cap according to claim 36, wherein said predetermined actions include at least one of deploying said collapsed ostomy bag, releasing gas from said cap, generating an indication for notifying a user of an increase in pressure, and generating an indication for notifying a user of a need to release gas.

38. A cap according to claim 1, wherein said safety mechanism is configured for releasing gas from a gas release mechanism.

39. A cap according to claim 1, wherein said safety mechanism includes an indication mechanism.

40. A cap according to claim 39, wherein said indication mechanism includes at least one of a visual indication, an audible indication, a mechanically activated protruding element configured to be seen by a user, an electrical indication configured to be perceived by a user, an electromechanical indication configured to be perceived by a user, a light, a vibration, a sound, a wireless signal, an instant message, an SMS transmission, and a Bluetooth signal.

41. A cap according to claim 36, wherein said action is configured to be ceased one of manually by a user and automatically by said control unit when the pressure decreases below a predetermined value.

42. A disposable cap according to claim 41, wherein said predetermined value is 30 mmHg.

43. A cap according to claim 36, wherein said logic algorithm is reprogrammable.

44. A cap according to claim 1, wherein said cap includes a gas filter.

45. A cap according to claim 1, wherein said safety mechanism is configured to allow at least a portion of said bag to unfurl by pushing of waste content discharging from a stoma.

46. A cap according to claim 45, wherein said safety mechanism is configured to allow a portion of said bag to unfurl and to allow a user to unfurl a furled portion of said bag.

47. A cap according to claim 46, wherein said bag includes one of a strap and a cord at one of a proximal and a distal end of said bag, said one of a strap and a cord configured to be pulled on by the user for unfurling said bag.

48. A method for relieving a pressure in an ostomy, comprising:
   sealing the ostomy with a cap, wherein the cap includes a collapsed ostomy bag;
   providing an automatic safety mechanism in the cap for automatically relieving a pressure in the cap above a predetermined pressure threshold by a change in safety mechanism position relative to said cap, said change permitting deployment of said bag;
   waiting for buildup of pressure within said cap; and
   manually actuating said change in safety mechanism position relative said cap to permit manual deployment of said bag.

49. A method according to claim 48, wherein said bag is configured to deploy when a pressure in said cap is above a preselected threshold.

50. A method according to claim 48, wherein said cap includes a separately openable cap-covering.

51. A method according to claim 48, wherein said cap includes a cap-covering, wherein said cap-covering is removable to allow deployment of said bag.

52. A method according to claim 51, wherein said safety mechanism is configured to eject said cap-covering when a pressure inside said cap reaches a predetermined value.

53. A method according to claim 48, wherein said safety mechanism is configured for pushing said bag out of said cap.

54. A method according to claim 48, wherein said safety mechanism includes an indication mechanism.

55. A cap according to claim 1, wherein said safety mechanism comprises a removable cover.

56. A cap according to claim 55, wherein said cover is ejectable by pressure from said bag pushing on said cover.

57. A cap according to claim 55, wherein said cover is releasable by a pressure sensing mechanism in said cap.

58. A cap for sealing a proximal opening in an ostomy port, including:
   a collapsed ostomy bag held within a housing of said cap, said bag being held to receive a pressure from within said proximal opening;
   wherein said cap includes an automatic safety mechanism comprising a cover positioned over said collapsed ostomy bag by attachment to a proximal end of said cap housing, the cover in said attached position blocking bag expansion beyond a proximal end of said cap;
   said safety mechanism being configured for automatic release of said cover from said expansion-blocking position to a release configuration upon a predetermined pressure being exerted upon said cover by pressure from said bag, due to said pressure received from within said proximal opening;
   wherein said release of said cover to said release configuration comprises at least partial detachment of said cover from said cap housing, permitting deployment of said bag to expand beyond said cap end, such that said pressure received from within said proximal opening is relieved; and
   said safety mechanism also being manually actuatable for manual release of said cover from said expansion-blocking position to said release configuration, permitting said deployment of said bag.

* * * * *